United States Patent
Fuentes-Ortega et al.

(10) Patent No.: US 10,945,626 B2
(45) Date of Patent: Mar. 16, 2021

(54) CATHETER WITH STAGGERED ELECTRODES SPINE ASSEMBLY

(71) Applicant: BIOSENSE WEBSTER (ISRAEL) LTD., Yokneam (IL)

(72) Inventors: Cesar Fuentes-Ortega, Pasadena, CA (US); Jamie Malinaric, New York, NY (US); Lior Botzer, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 293 days.

(21) Appl. No.: 15/890,309

(22) Filed: Feb. 6, 2018

(65) Prior Publication Data

US 2019/0239765 A1 Aug. 8, 2019

(51) Int. Cl.
*A61B 5/042* (2006.01)
*A61B 5/00* (2006.01)
*A61M 25/01* (2006.01)
*A61B 5/06* (2006.01)

(52) U.S. Cl.
CPC .......... *A61B 5/0422* (2013.01); *A61B 5/6859* (2013.01); *A61B 5/062* (2013.01); *A61M 25/0147* (2013.01)

(58) Field of Classification Search
CPC .................................................. A61B 5/0422
See application file for complete search history.

(56) References Cited

U.S. PATENT DOCUMENTS

| | | | |
|---|---|---|---|
| 5,782,239 A * | 7/1998 | Webster, Jr. | A61B 5/0422 600/374 |
| 7,089,045 B2 | 8/2006 | Fuimaono et al. | |
| 7,155,270 B2 | 12/2006 | Solis et al. | |
| 7,228,164 B2 | 6/2007 | Fuimaono et al. | |
| 7,276,062 B2 | 10/2007 | McDaniel et al. | |
| 7,302,285 B2 | 11/2007 | Fuimaono et al. | |
| 7,524,318 B2 | 4/2009 | Young et al. | |
| 8,825,130 B2 * | 9/2014 | Just | A61B 18/1492 600/374 |
| 8,920,369 B2 | 12/2014 | Salahieh et al. | |
| 9,820,664 B2 * | 11/2017 | Hoitink | A61B 5/6858 |

(Continued)

FOREIGN PATENT DOCUMENTS

| | | |
|---|---|---|
| EP | 3 023 052 A1 | 5/2016 |
| EP | 3 040 042 A1 | 7/2016 |
| EP | 3 207 867 A1 | 8/2017 |

OTHER PUBLICATIONS

ISA International Search Report dated Mar. 28, 2019 for International Patent Application No. PCT/US2019/016580, 5 pages.
ISA Written Opinion dated Mar. 28, 2019 for International Patent Application No. PCT/US2019/016580, 7 pages.
ISA International Preliminary Report on Patentability dated Aug. 11, 2020 for International Patent Application No. PCT/US2019/016580, 6 pages.

*Primary Examiner* — Lee S Cohen
(74) *Attorney, Agent, or Firm* — Lewis Roca Rothgerber Christie LLP

(57) ABSTRACT

An electrophysiology catheter with a distal electrode assembly having covered spine carrying a plurality of microelectrodes. The position of the microelectrodes on each spine is staggered relative to microelectrodes on adjacent spines so as to minimize the risk of electrodes on adjacent spines touching each other during use of the catheter. The staggered electrode configuration provides the distal electrode assembly with a greater effective contact surface because the effective concentric electrode arrays is increased or at least doubled.

20 Claims, 30 Drawing Sheets

(56) References Cited

U.S. PATENT DOCUMENTS

| | | |
|---|---|---|
| 2013/0253504 A1* | 9/2013 | Fang .................. A61B 18/1492 606/41 |
| 2014/0194716 A1* | 7/2014 | Diep .................. A61B 18/1492 600/374 |
| 2014/0303618 A1 | 10/2014 | Wu et al. |
| 2014/0350462 A1 | 11/2014 | Ataollahi et al. |
| 2016/0206361 A1 | 7/2016 | Jadhav et al. |
| 2018/0249928 A1* | 9/2018 | Mangual-Soto ..... A61B 5/0537 |

\* cited by examiner

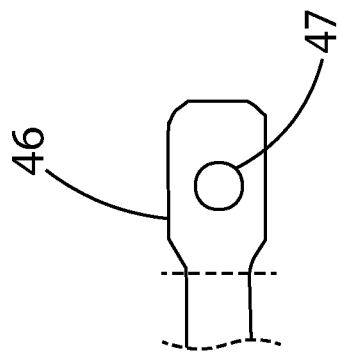
FIG. 6D
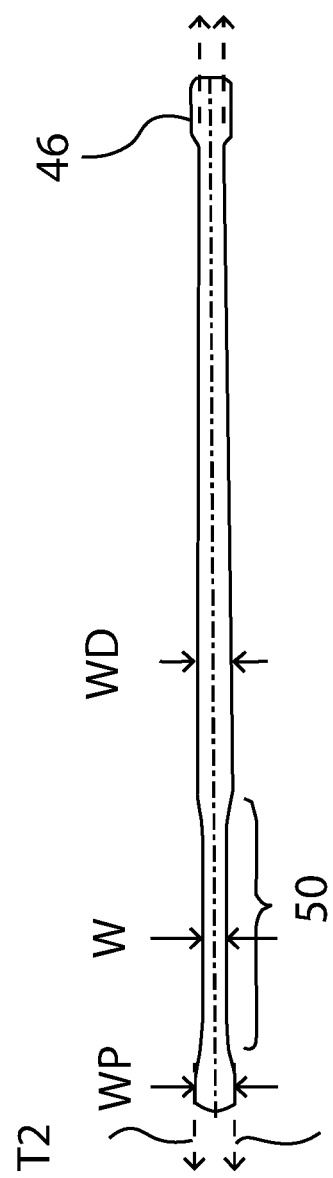
FIG. 6C
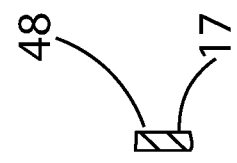
FIG. 6G
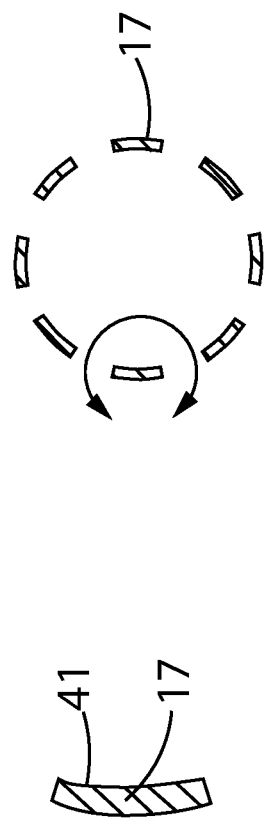
FIG. 6E
FIG. 6F

CATHETER WITH STAGGERED ELECTRODES SPINE ASSEMBLY

FIELD OF INVENTION

This invention relates to an electrophysiology catheter, in particular, a cardiac electrophysiology catheter with an electrode configuration that provides for more accurate and discrete sensing of fractionated signals.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Once the catheter is positioned within the heart, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with the endocardium. By monitoring the electrical signals at the endocardium, aberrant conductive tissue sites responsible for the arrhythmia can be pinpointed.

For sensing by ring electrodes mounted on a catheter, lead wires transmitting signals from the ring electrodes are electrically connected to a suitable connector in the distal end of the catheter control handle, which is electrically connected to an ECG monitoring system and/or a suitable 3-D electrophysiology (EP) mapping system, for example, CARTO, CARTO XP or CARTO 3, available from Biosense Webster, Inc. of Irwindale, Calif.

Smaller and more closely-spaced electrode pairs allow for more accurate detection of near-field potentials versus far-field signals, which can be very important when trying to treat specific areas of the heart. For example, near-field pulmonary vein potentials are very small signals whereas the atria, located very close to the pulmonary vein, provide much larger signals. Accordingly, even when the catheter is placed in the region of a pulmonary vein, it can be difficult for the electrophysiologist to determine whether the signal is a small, close potential (from the pulmonary vein) or a larger, farther potential (from the atria). Smaller and closely-spaced bipoles permit the physician to more accurately remove far field signals and obtain a more accurate reading of electrical activity in the local tissue. Accordingly, by having smaller and closely-spaced electrodes, one is able to target exactly the locations of myocardial tissue that have pulmonary vein potentials and therefore allows the clinician to deliver therapy to the specific tissue. Moreover, the smaller and closely-spaced electrodes allow the physician to determine the exact anatomical location of the ostium/ostia by the electrical signal.

Increasing electrode density (for example, by increasing the plurality of electrodes carried on the catheter) also improves detection accuracy. However, the more electrodes that are carried on the catheter, especially with higher electrode density, the risk of electrodes touching and shorting increases. Moreover, there is always the desire to improve electrode tissue contact with highly-flexible electrode assembly structures that can make contact reliably but in a manner whereby the electrode-carrying structures behave in a controllable and predictable manner without perforating or injuring tissue. As the materials used to construct these structures become more flexible and delicate, the risk of deformation and, in particular, elongation of the smaller ring electrodes and their supporting structure during catheter assembly increases. Furthermore, as electrode assembly structures become more delicate, the risk of components detaching, kinking and tangling increases.

It has also been observed that signal acquisition through electrodes is adversely affected when electrodes touch or come in contact with each other. Contact and collision can occur during mapping when the operator is manipulating a distal electrode assembly of the catheter, especially when the operator "sweeps" the assembly along tissue surface. Contact and collision between electrodes can create artifacts which adversely impact the quality of ECG signals and map generation.

Accordingly, a need exists for an electrophysiology catheter with closely-spaced microelectrodes for high electrode density. There is also a need for an electrophysiology catheter having electrode-carrying structures that are delicate in construction to provide desired flexible yet be predictable in their movement upon tissue contact. There is a further need for an electrophysiology catheter that minimizes the risk of electrodes touching and shorting.

SUMMARY OF THE INVENTION

The present invention is directed to an electrophysiology catheter with a distal electrode assembly carrying very small and closely-spaced microelectrodes on a plurality of divergent spines that can flexibly spread over tissue surface area for simultaneously detecting signals at multiple locations with minimized detection of undesirable noise, including far-field signals. The distal electrode assembly is configured to conform to different anatomies of tissue in the atrial cavities of the heart. The spines have curved segments or curved segments with linear segments for a wide range of adaptability to different tissue surfaces while providing mechanical advantages at distinct segments for improved flexibility and rigidity to facilitate better tissue contact. Each spine has a generally tapering configuration from its proximal end to its distal end for providing a stronger, more rigid proximal base and more flexible distal ends for improved flexibility characteristics while minimizing the risk of spines touching or entangling.

In some embodiments, an electrophysiology catheter has an elongated body and a distal electrode assembly. The distal electrode assembly has a proximal stem, a plurality of spines emanating from the stem and a plurality of nonconductive spine covers, each surrounding a respective spine, each spine cover having a plurality of tensile members embedded in a sidewall of the cover.

In some embodiments, the tensile members extend in the longitudinal direction.

In some embodiments, the tensile members have a portion extending in the longitudinal direction.

In some embodiments, the tensile members include wires.

In some embodiments, tensile members include fibers.

In some embodiments, an electrophysiology catheter has an elongated body and a distal electrode assembly. The distal electrode assembly has a proximal stem and a plurality of spines, each spine having an enlarged distal portion, the enlarged distal portion having a through-hole. The distal electrode assembly also has a plurality of nonconductive spine covers, each surrounding a respective spine. The distal electrode assembly further has a cap cover encapsulating the enlarged distal portion, the cap cover having a portion extending through the through-hole.

In some embodiments, an electrophysiology catheter has an elongated body and a distal electrode assembly. The distal electrode assembly has a proximal stem and a plurality of at least eight spines, each spine having a first section with a first preformed curvature defined by a first radius, and a linear section. The distal electrode assembly also has a plurality of nonconductive spine covers and a plurality of microelectrodes, with at least one microelectrode on each spine.

In some embodiments, each spine includes a second section with a second preformed curvature defined by a second radius different from the first radius, the second section with the second preformed curvature being distal of the first section with the first preformed curvature.

In some embodiments, the first radius is smaller than the second radius.

In some embodiments, the second preformed curvature is opposite of the first preformed curvature.

In some embodiments, the second section with the second preformed curvature is distal of the first section with the first preformed curvature.

In some embodiments, the linear section is between the first section with the first preformed curvature and the second section with the second preformed curvature.

In some embodiments, the first section with the linear section is distal of the second section with the second preformed curvature.

In some embodiments, each covered spine has an outer circumference less than 3 french.

In some embodiments, the outer circumference is about 2.6 french.

In some embodiments, an electrophysiology catheter has an elongated body, and a distal electrode assembly. The distal electrode assembly has a proximal portion, and a plurality of spines, each spine having a linear taper with a wider proximal end and a narrower distal end. The distal electrode assembly also has a plurality of nonconductive spine covers, each nonconductive spine cover surrounding a respective spine.

In some embodiments, the linear taper is continuous.

In some embodiments, the linear taper is noncontinuous.

In some embodiments, the noncontinuous linear taper includes an indented portion with a width lesser than a width of a more proximal stem and a width of a more distal portion.

In some embodiments, a spine has a hinge along a lateral edge configured for in-plane deflection of the spine.

In some embodiments, an electrophysiology catheter has an elongated body and a distal electrode assembly. The distal electrode assembly has a proximal stem, a plurality of at least eight spines, each spine having a linear taper with a wider proximal end and a narrower distal end. The distal electrode assembly also has a plurality of nonconductive spine covers, each nonconductive cover surrounding a respective spine. The distal electrode assembly further has a plurality of microelectrodes, the plurality being at least about 48, each microelectrode having a length of about 480 µm.

In some embodiments, the microelectrodes on each spine are separated by a distance ranging between about 1 mm and 3 mm, as measured between leading edges of the microelectrodes.

In some embodiments, the distance is about 2 mm.

In some embodiments, the microelectrodes on each spine are arranged as bipole pairs, with leading edges of microelectrodes within a pair separated by a first distance ranging between about 1 mm and 3 mm, and with leading edges of leading microelectrodes between pairs separated by a second distance ranging between 1 mm and 6 mm.

In some embodiments, the first distance is about 2 mm and the second distance is about 6 mm.

In some embodiments, the plurality of microelectrodes equals about 64.

In some embodiments, the plurality of microelectrodes equals about 72.

In some embodiments, a first ring electrode is carried on the proximal stem of the distal electrode assembly, and a second and a third ring electrodes carried on a distal portion of the elongated body.

In some embodiments, an electrophysiology catheter has an elongated body, and a distal electrode assembly. The distal electrode assembly has a proximal stem defining a circumference around the longitudinal axis. The distal electrode assembly also has a plurality of spines emanating from the proximal stem and diverging at their distal ends, the plurality of spines alternating between first spines and second spines around the circumference of the stem. The distal electrode assembly further has a plurality of nonconductive spine covers, each spine cover surrounding a respective spine, and a plurality of microelectrodes having a staggered configuration on the first spines and the second spines, wherein a most proximal microelectrode on each first spine is positioned at a greater distance from the proximal stem, and a most proximal electrode on each second spine is positioned at a lesser distance from the proximal stem.

The staggered electrode configuration provides the distal electrode assembly with a greater effective contact surface because the effective concentric electrode arrays is increased or at least doubled.

In some embodiments, the distal electrode assembly comprises at least four first spines and four second spines, and each spine carries eight microelectrodes.

In some embodiments, each microelectrode has a length of about 480 µm.

In some embodiments, the microelectrodes on each spine are separated by a distance ranging between about 1 mm and 3 mm, as measured between leading edges of the microelectrodes.

In some embodiments, the distance is about 2 mm.

In some embodiments, the microelectrodes on each spine are arranged as bipole pairs, with leading edges of microelectrodes within a pair separated by a first distance ranging between about 1 mm and 3 mm, and with leading edges of leading microelectrodes between pairs separated by a second distance ranging between 1 mm and 6 mm.

In some embodiments, the first distance is about 2 mm and the second distance is about 6 mm.

In some embodiments, an electrophysiology catheter has an elongated body and a distal electrode assembly. The distal electrode assembly has a support structure with a proximal stem having a side wall having an inner surface defining a lumen, the side wall having an opening. The support structure also has a plurality of spines emanating from the proximal stem and diverging at their distal ends, and a plurality of nonconductive cover, each nonconductive cover surrounding a respective spine. The distal electrode assembly further has a plurality of microelectrodes on each spine, and a housing insert received in the lumen of the stem, the housing insert having an outer surface leaving a void between the outer surface and the inner surface of the stem. An adhesive fills the void between the inner surface of the proximal stem and the outer surface of the housing insert, the adhesive having a portion passing through the opening in the sidewall of the proximal stem.

In some embodiments, the housing insert has a lumen with a cross-section having an elongated kidney bean-shaped configuration.

In some embodiments, the housing insert has a lumen with a cross-section having a C-shaped configuration.

In some embodiments, the opening in the proximal stem provides visual access into the lumen of the stem for inspection of components extending therethrough during assembly. Moreover, the adhesive filling the void is injected or otherwise applied through the opening.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 6C is a detailed view of a distal portion of the spine of FIG. 6B.

FIG. 6D is a detailed view of an enlarged distal portion of a spine of FIG. 6A.

FIG. 6E is an end cross-sectional view of the unibody support member of FIG. 6B, taken along line E-E.

FIG. 6F is a detailed view of an end cross-sectional view of a proximal portion of the spine of FIG. 6B.

FIG. 6G is a detailed view of an end cross-sectional view of a distal portion of the spine of FIG. 6B.

DETAILED DESCRIPTION OF THE INVENTION

Figure 1:
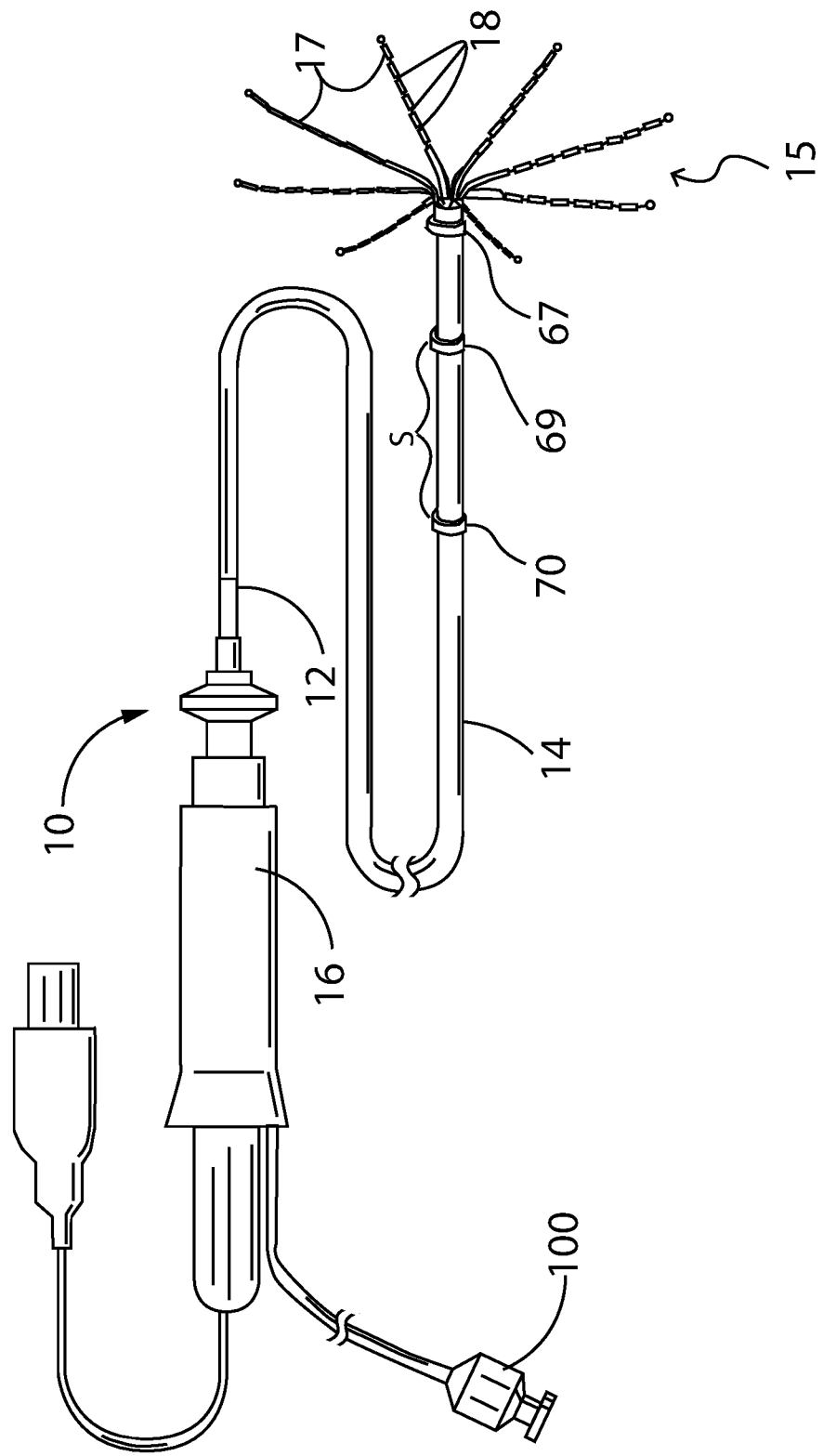
FIG. 1 is a perspective view of a catheter of the present invention, according to one embodiment.

Referring to FIG. 1, in some embodiments of present invention, a catheter 10 includes a catheter body 12, an intermediate deflection section 14, a distal electrode assembly 15, and a control handle 16 proximal of the catheter body 12. The distal electrode assembly 15 includes a plurality of spines 17, with each spine supporting a plurality of microelectrodes 18.

Figure 2:
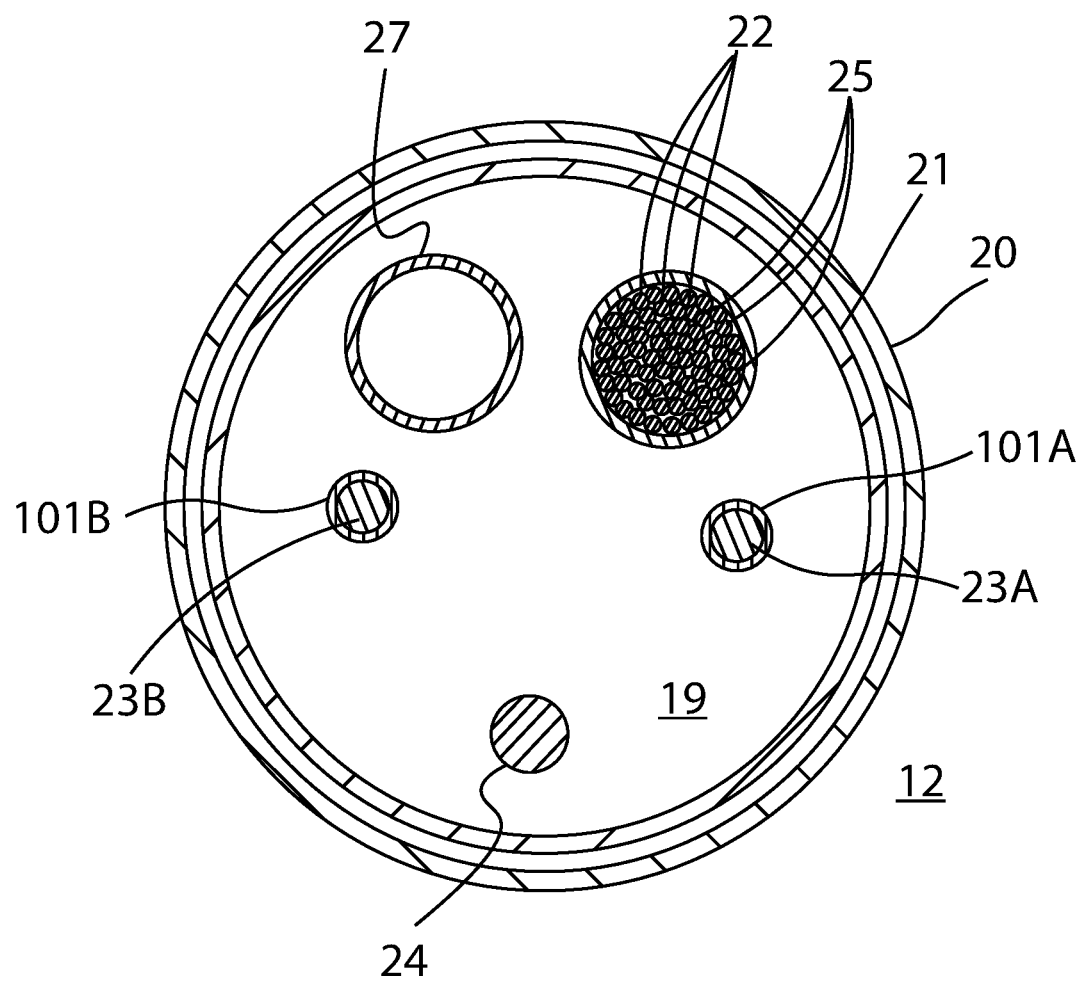
FIG. 2 is an end cross-sectional view of a catheter body of the catheter of FIG. 1.

In some embodiments, the catheter body 12 comprises an elongated tubular construction, having a single, axial or central lumen 19, as shown in FIG. 2. The catheter body 12 is flexible, i.e., bendable, but substantially non-compressible along its length. The catheter body 12 can be of any suitable construction and made of any suitable material. A presently preferred construction comprises an outer wall 20 made of a polyurethane, or PEBAX. The outer wall 20 comprises an imbedded braided mesh of high-strength steel, stainless steel or the like to increase torsional stiffness of the catheter body 12 so that, when the control handle 16 is rotated, the deflection section 14 of the catheter 10 rotates in a corresponding manner.

The outer diameter of the catheter body 12 is not critical. Likewise the thickness of the outer wall 20 is not critical, but is thin enough so that the central lumen 19 can accommodate components, including, for example, one or more puller wires, electrode lead wires, irrigation tubing, and any other wires and/or cables. In some embodiments, the inner surface of the outer wall 20 is lined with a stiffening tube 21, which can be made of any suitable material, such as polyimide or nylon. The stiffening tube 21, along with the braided outer wall 20, provides improved torsional stability while at the same time minimizing the wall thickness of the catheter, thus maximizing the diameter of the central lumen 19. As would be recognized by one skilled in the art, the catheter body construction can be modified as desired. For example, the stiffening tube can be eliminated.

Figure 3:
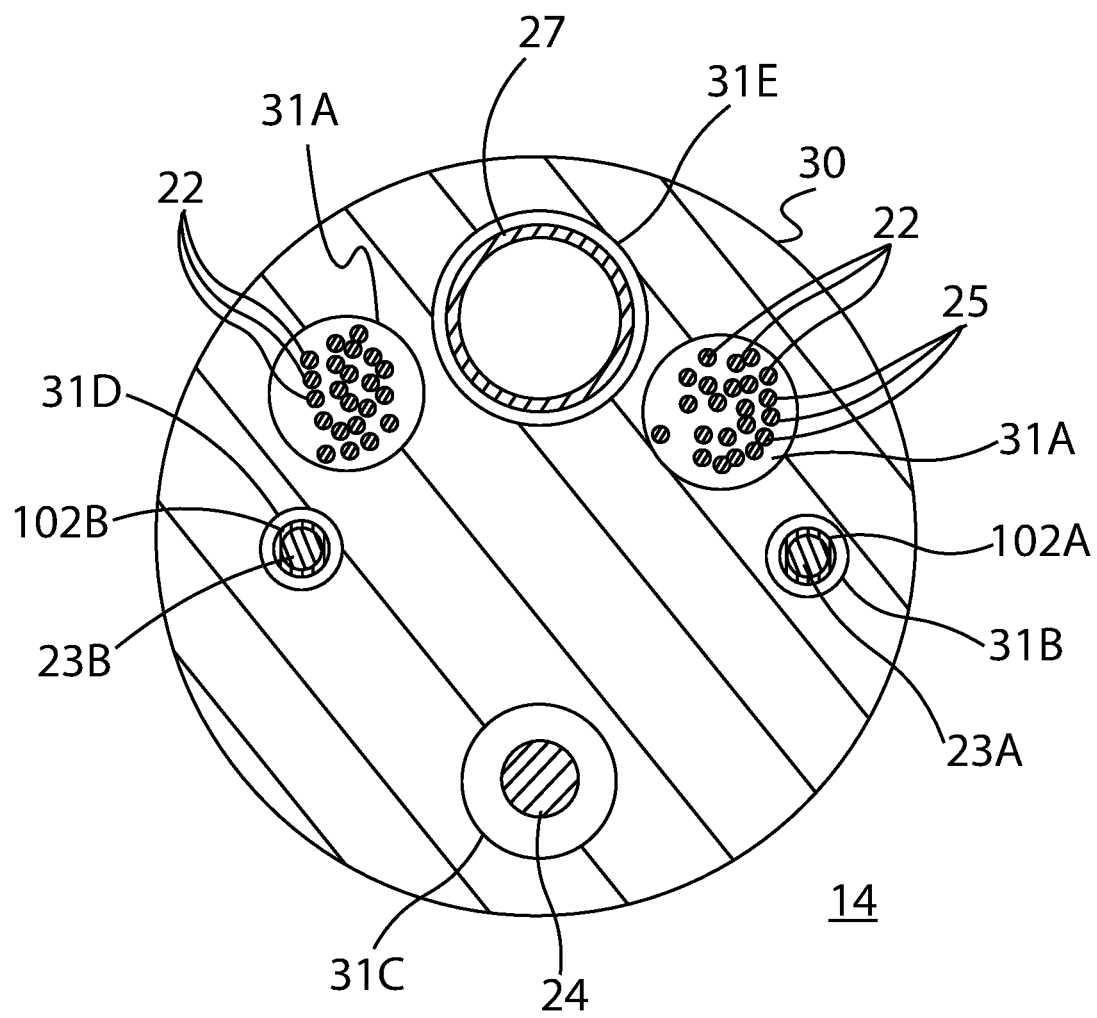
FIG. 3 is an end cross-sectional view of a deflection section of the catheter of FIG. 1

In some embodiments, the intermediate deflection section comprises a shorter section of tubing 30, which as shown in FIG. 3, has multiple lumens 31. In some embodiments, the tubing 30 is made of a suitable biocompatible material more flexible than the catheter body 12. A suitable material for the tubing 30 is braided polyurethane, i.e., polyurethane with an embedded mesh of braided high-strength steel, stainless steel or the like. The outer diameter of the deflection section 14 is similar to that of the catheter body 12. The plurality and size of the lumens are not critical and can vary depending on the specific application.

Various components extend through the catheter 10. In some embodiments, the components include lead wires 22 for the distal electrode assembly 15, one or more puller wires 23A and 23B for deflecting the deflection section 14, a cable 24 for an electromagnetic position sensor 26 (see FIG. 14A and FIG. 15A) housed at or near a distal end of the deflection section 14. In some embodiments, the catheter includes an irrigation tubing 27 for passing fluid to the distal end of the deflection section 14. These components pass through the central lumen 19 of the catheter body 12, as shown in FIG. 2.

In the deflection section 14, different components pass through different lumens 31 of the tubing 30 as shown in FIG. 3. In some embodiments, the lead wires 22 pass through one or more lumens 31A, the first puller wire 23A passes through lumen 31B, the cable 24 passes through lumen 31C, the second puller 23B passes through lumen 31D, and the irrigation tubing 27 passes through lumen 31E. The lumens 31B and 31D are diametrically opposite of each other to provide bi-directional deflection of the intermediate deflection section 14. Additional components can pass through additional lumens or share a lumen with the other aforementioned components, as needed.

Figure 4:
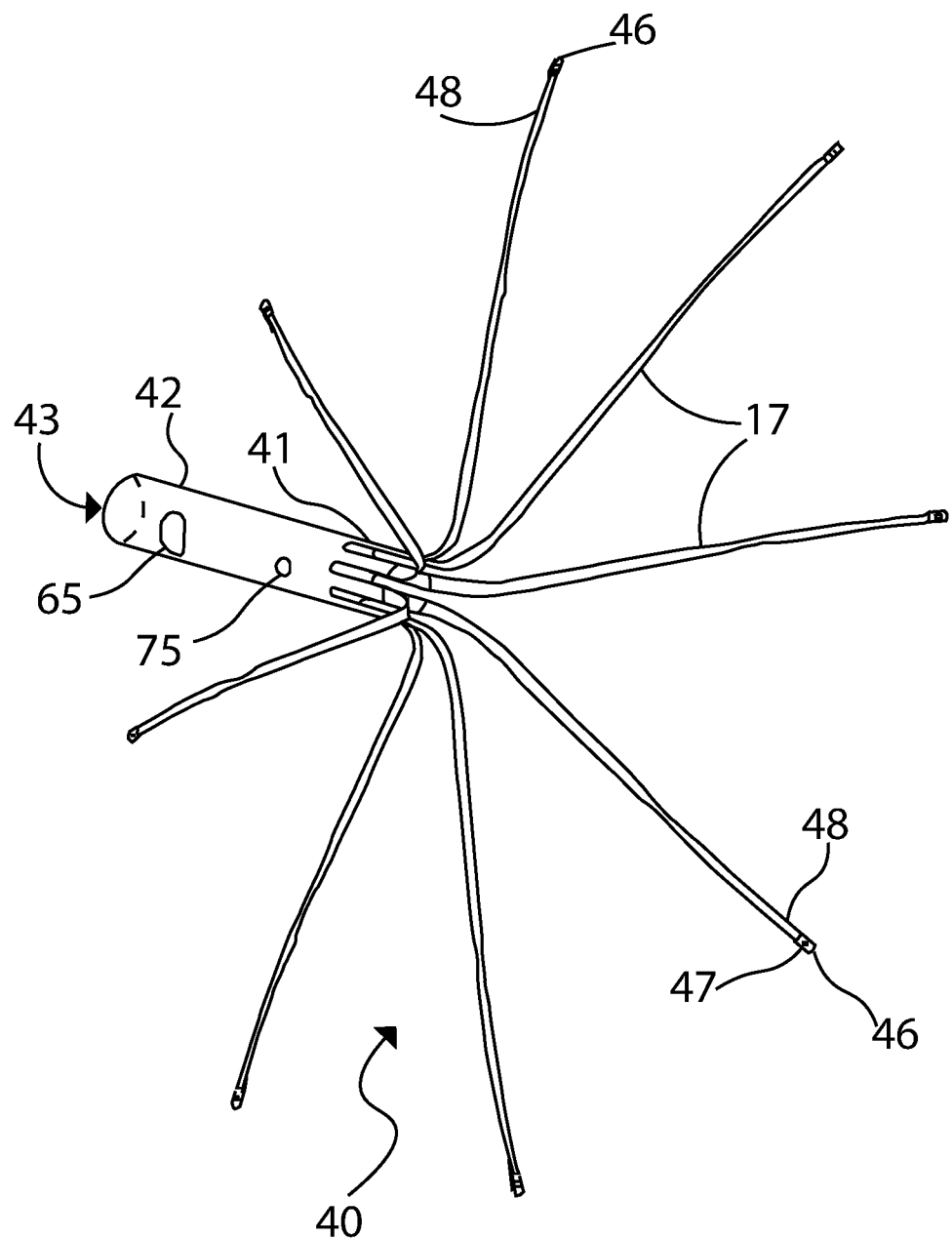
FIG. 4 is a perspective view of a unibody support member, according to one embodiment.
Figure 5A:
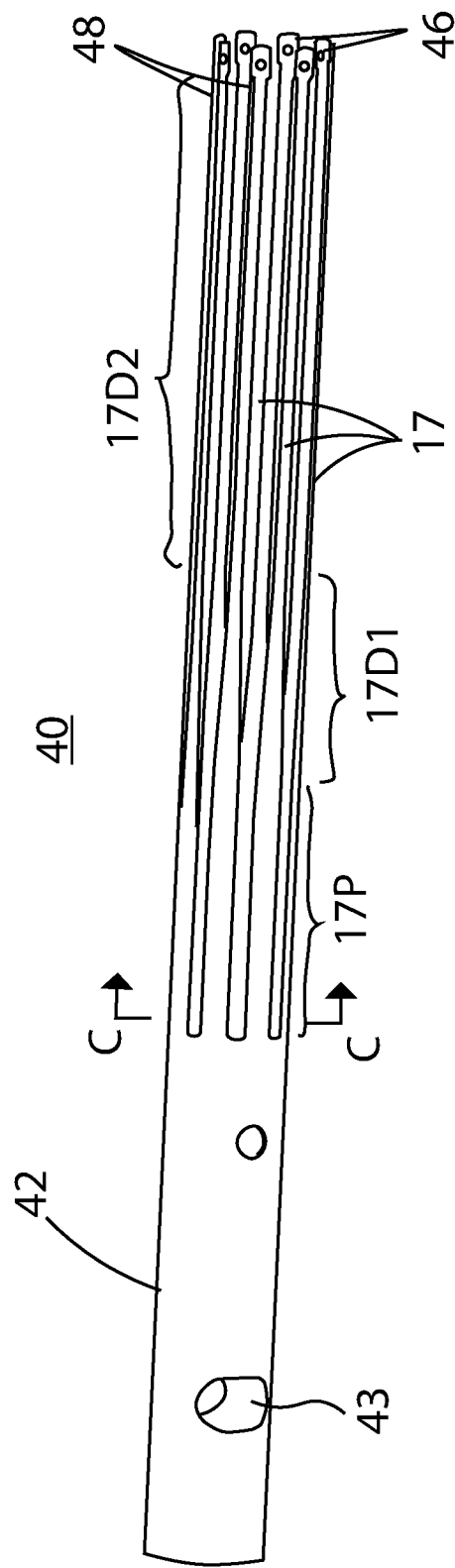
FIG. 5A is a side view of a unibody support member, according to one embodiment.
Figure 5B:
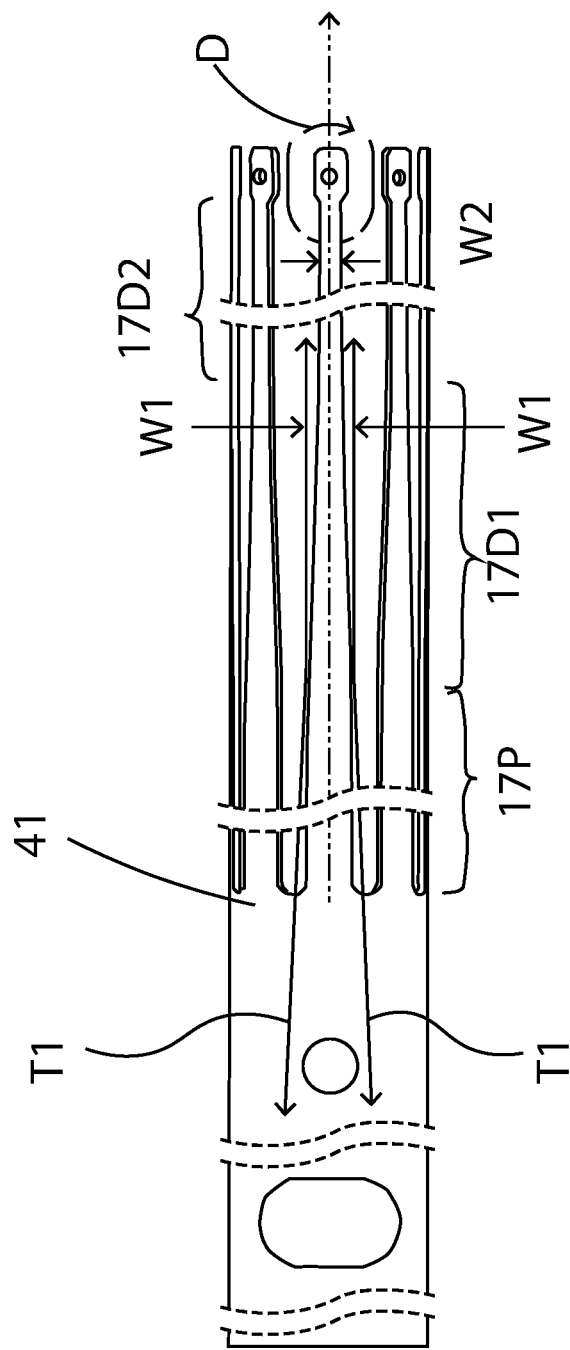
FIG. 5B is a detailed view of the unibody support member of FIG. 5A.
Figure 5C:
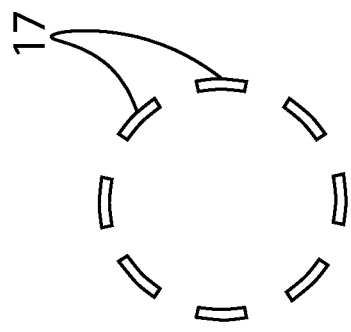
FIG. 5C is an end cross-sectional view of the unibody support member of FIG. 5A, taken a line C-C.
Figure 5E:
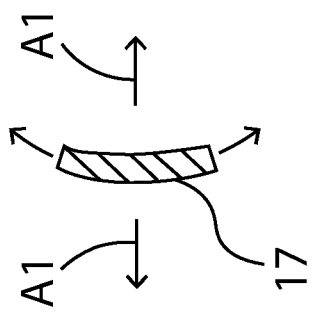
FIG. 5E is a detailed view of an end cross-sectional view of a spine of FIG. 5A.
Figure 5D:
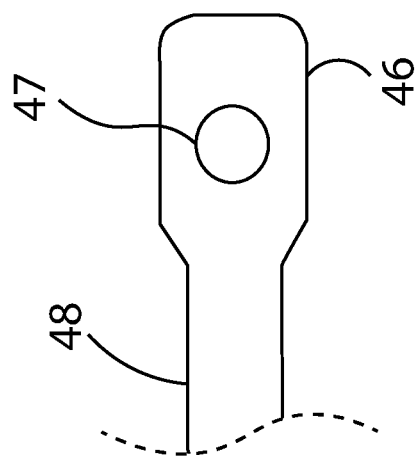
FIG. 5D is a detailed view of an enlarged distal portion of a spine of FIG. 5A.
Figure 6A:
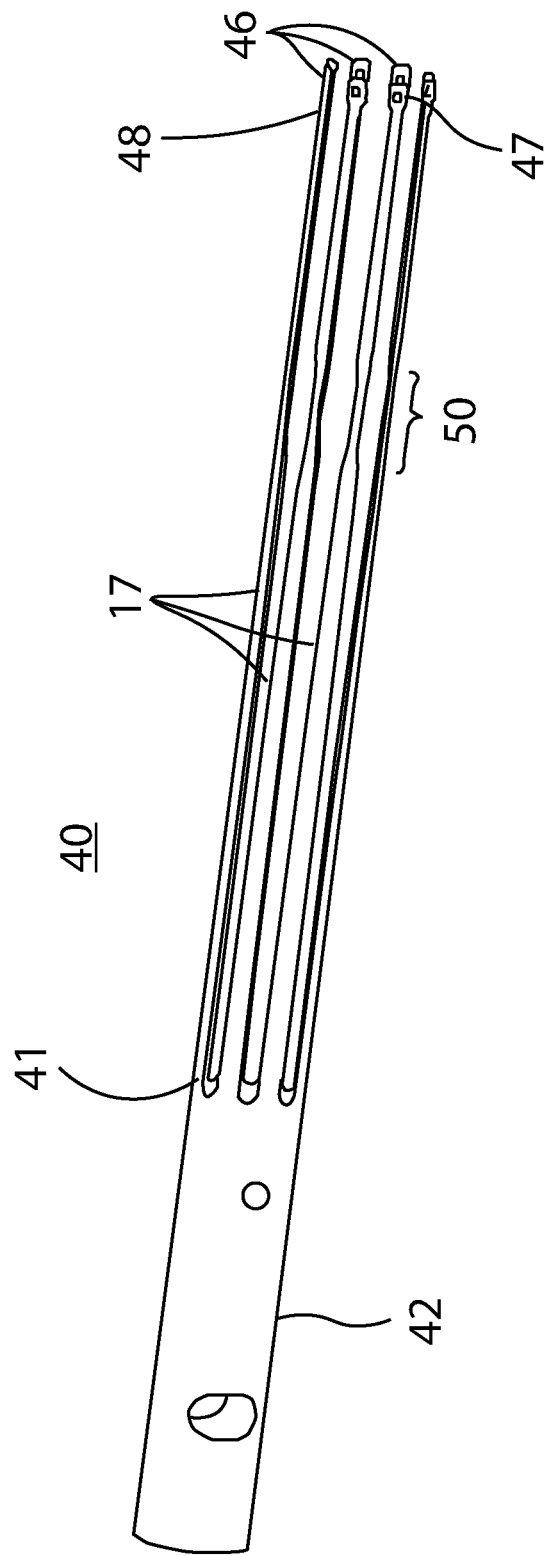
FIG. 6A is a side view of a unibody support member, according to one embodiment.
Figure 6B:
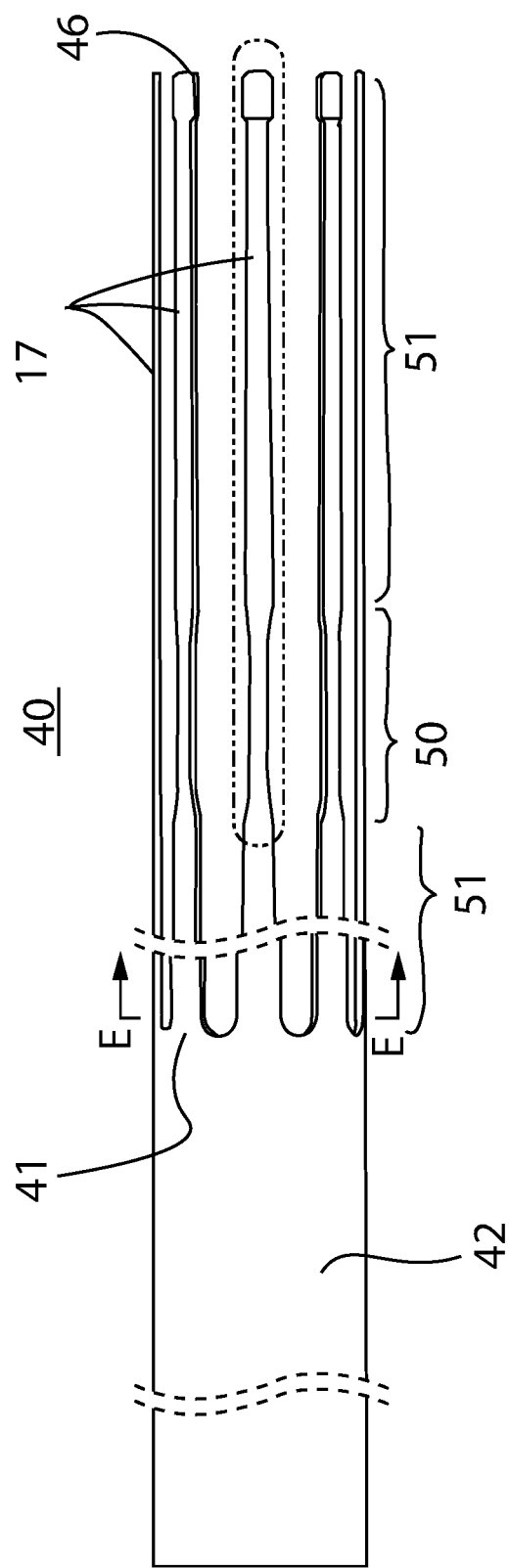
FIG. 6B is a detailed view of the unibody support member of FIG. 6A.

Distal of the deflection section 14 is the distal electrode assembly 15 which includes a unibody support member 40 as shown in FIG. 4. In some embodiments, the unibody support member 40 comprises a superelastic material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability.

In some embodiments, the member 40 is constructed and shaped from an elongated hollow cylindrical member, for example, with portions cut (e.g., by laser cutting) or otherwise removed, to form a proximal portion or stem 42 and the elongated bodies of the spines 17 which emanate from the stem longitudinally and span outwardly from the stem. The stem 42 defines a lumen 43 therethrough for receiving a distal end portion 30D of the multi-lumened tubing 30 (see FIG. 14A) of the deflection section 14, and various components, as further discussed below, which are either housed in the stem 42 or extend through the lumen 43.

Each spine 17 of the member 40 has an enlarged distal portion 46, and each spine has a wider proximal end and a narrower distal end. In some embodiments, as shown in FIG. 5A, FIG. 5B, FIG. 5C, FIG. 5D and FIG. 5E, the spine is linearly tapered for "out-of-plane" flexibility that varies along it length (see arrows A1 in FIG. 5E), including flexibility that increases toward the distal end 48. In some embodiment, one or more spines 17 have a proximal portion 17P with a uniform width W1, a distal portion 17D1 with continuous linear taper defined by taper lines T1 (see FIG. 5B), and a more distal portion 17D2 with a uniform width W2<W1. The distal portions 17D1 has a continuously gradual increase in flexibility so that the spines can adopt a predetermined form or curvature when the distal portions 46 come into contact with tissue. The resulting spines with a relatively more rigid proximal portion and a relatively more flexible distal portion help prevent the spines from crossing and overlapping each other during use.

In some embodiments, one or more spines 17 have a noncontinuous linear taper between the ends 41 and 46, as shown in FIG. 6A, FIG. 6B, FIG. 6C, FIG. 6D, FIG. 6E, FIG. 6F and FIG. 6G. The noncontinuous linear taper includes one or more narrower or indented portions 50 that are strategically positioned along the spine to interrupt an otherwise continuous linear taper, defined by taper T2 between the stem 42 and the enlarged distal portion 46. Each indented portion 50 has a width W (see FIG. 6C) that is lesser than the width WD of a more distal portion and also lesser than the width WP of a more proximal portion where width WD<width WP. Each indented portion 50 thus advantageously allows that region of the spine to have a different flexibility than immediately adjacent (distal and proximal) portions 51 of the spine, and to provide a degree of independent flexibility between the portions separated by the indented portion 50 (see FIG. 6B). Accordingly, these spines are allowed to exhibit markedly greater flexibility and hence tighter or more acute curvatures in the region of the indented portions 50 relative to the portions 51 of the spines when the distal portions 46 come into contact with tissue.

In some embodiments, each spine (between the distal end of the stem 42 and the distal end of the spine) has a length ranging between about 1.0 cm to 2.5 cm, or between about 1.50 cm and 2.0 cm, a width ranging between about 0.009 inches and 0.02 inches. In some embodiments, the indented portion 50 has a length ranging between about 10%-20% of the length of the spine, and a width W ranging between about 50%-80% of immediately adjacent widths, with its leading proximal edge located at about 55%-65% of the length of the spine, measured from the distal end of stem 42.

Figure 7A:
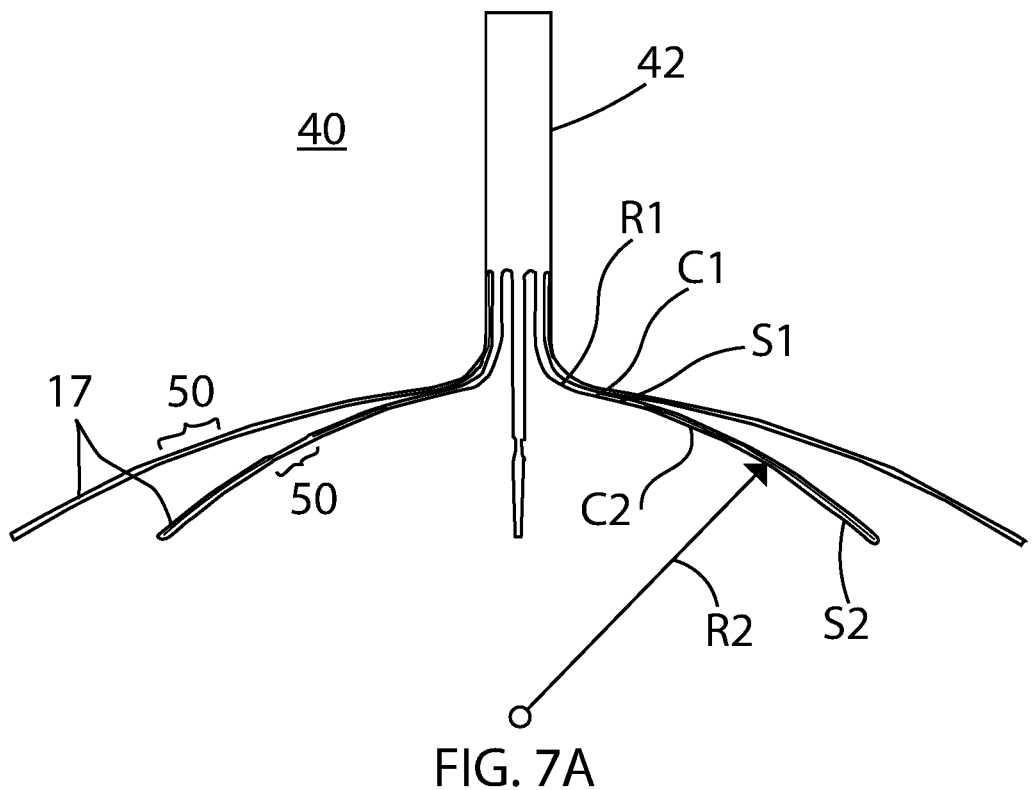
FIG. 7A is a side view of a unibody support member, according to one embodiment.
Figure 7B:
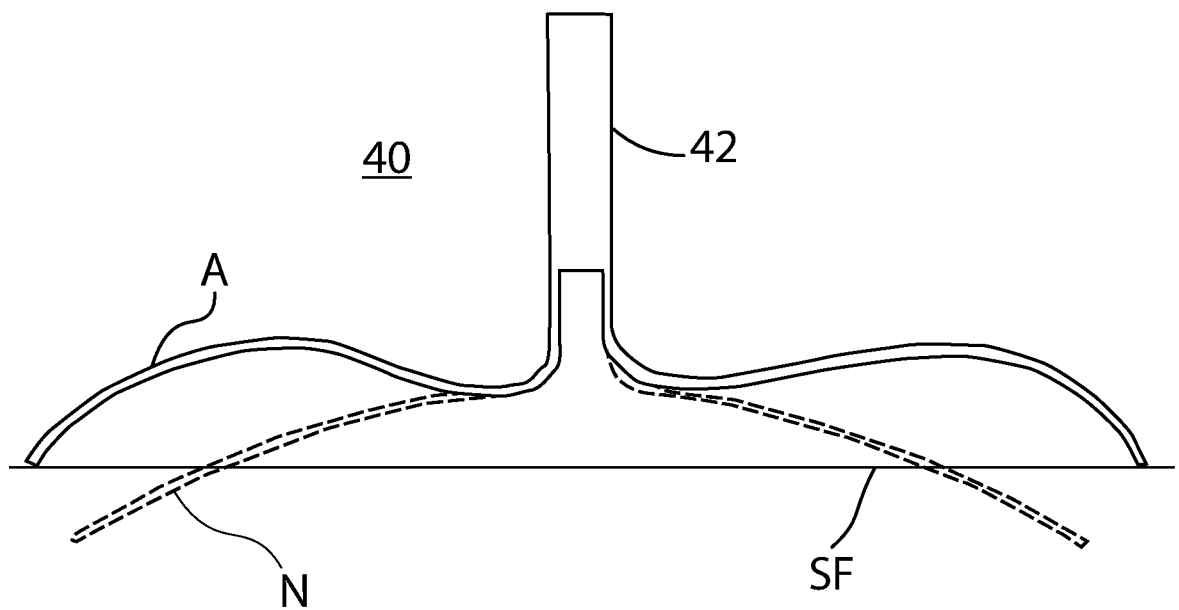
FIG. 7B is a side view of the unibody support member of FIG. 7A, in tissue contact.

To further facilitate microelectrode contract with tissue along the entire length of the spine, each spine 17 has a preformed configuration or curvature, accomplished by, for example, heat and a molding fixture. One or more spines 17 have at least two different preformed curvatures C1 and C2, as shown in FIG. 7A, with segment S1 with preformed curvature C1 defined by radius R1 and segment S2 with preformed curvature C2 defined by radius R2, wherein radius R1<R2 and the curvatures C1 and C2 are generally in opposition direction of each other so that the spines of the unibody support member 40 has a generally forward-facing concavity that resembles an open umbrella. As shown in FIG. 7B (with only two spines shown for purposes of clarity), when the spine distal ends come in contact with an illustrative surface SF, the preformed spines transition from their neutral configuration N (shown in broken lines) into their adaptive or temporarily "deformed" configuration A which may include a "crouched" profile (compared to their neutral configuration) that may be better suited for a region of heart tissue with undulations. Advantageously, the unibody support member 40 maintains its generally forward-facing concave configuration without turning inside out upon tissue contact, like an umbrella upturning in strong wind.

Figure 8A:
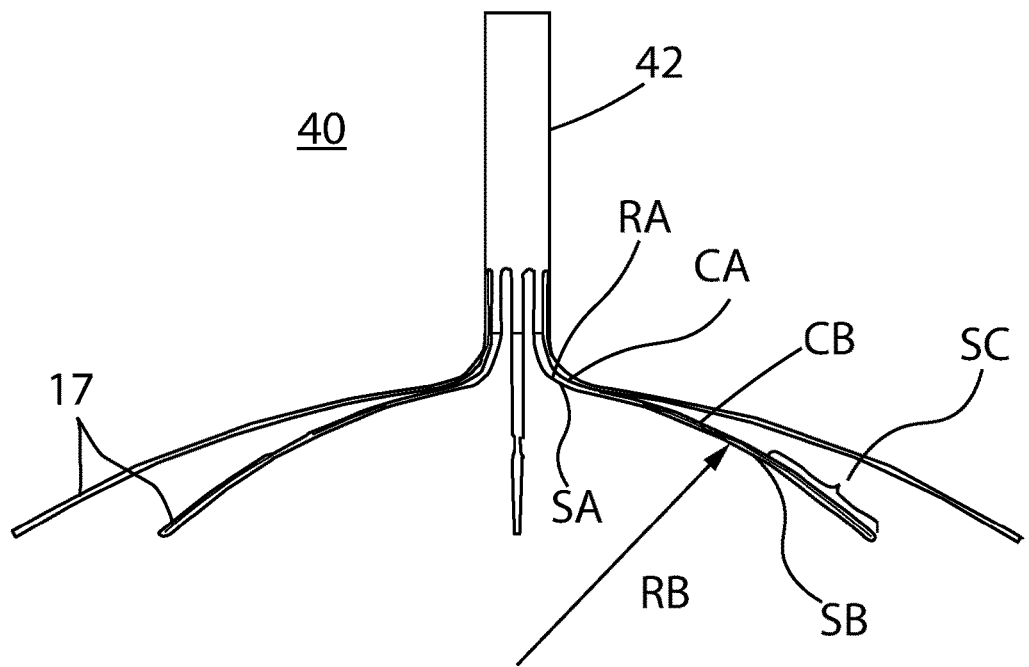
FIG. 8A is a side view of a unibody support member, according to another embodiment.
Figure 8B:
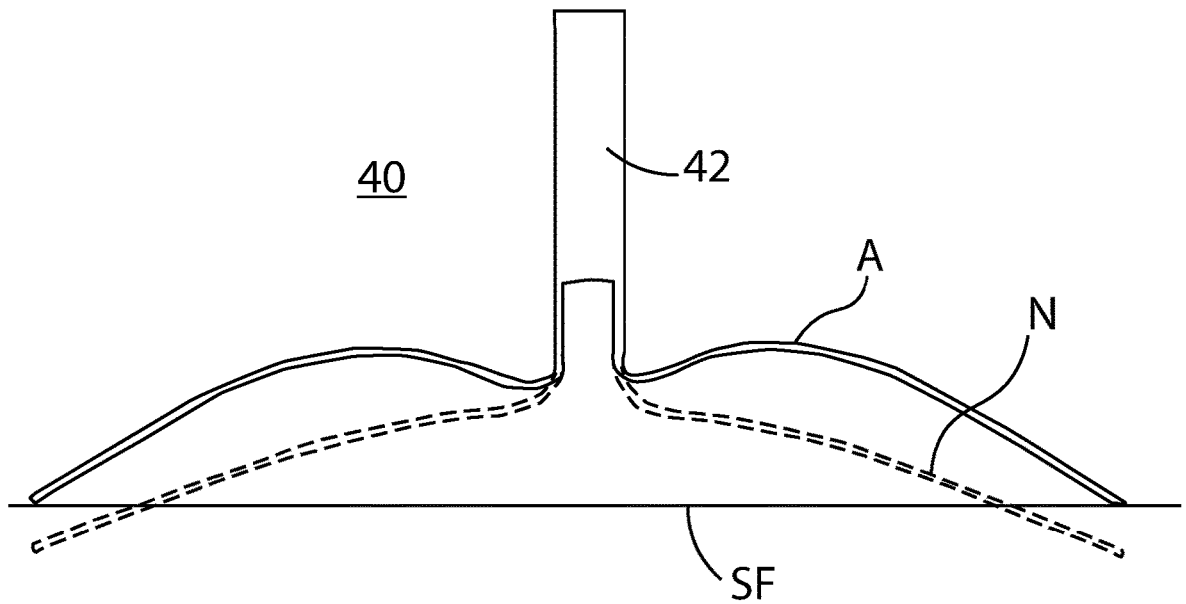
FIG. 8B is a side view of the unibody support member of FIG. 8A, in tissue contact.

In some embodiments, one or more spines 17 have at least a curved segment and a linear segment. In some embodiments, one or more spines have at least two different preformed curvatures along its length. For example, as shown in FIG. 8A, one or more spines 17 have a first segment SA with preformed curvature CA defined by radius RA, a second segment SB with preformed curvature CB defined by radius RB, and a third segment SC that is linear, wherein radius RA<radius RB. As shown in FIG. 8B (with only two spines shown for purposes of clarity), when the spine distal ends come in contact with an illustrative surface SF, the preformed spines transition from their neutral configuration N into their adaptive or temporarily "deformed" configuration A which may include a deeper concavity (compared to their neutral configuration) that may be better suited for a region of heart tissue with a convexity.

Figure 9A:
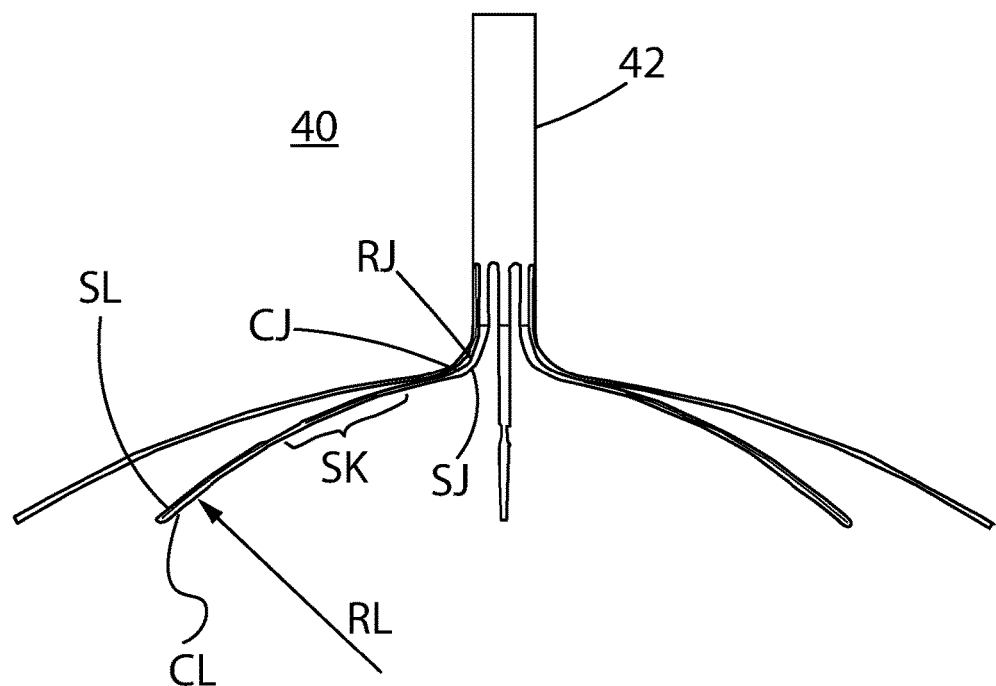
FIG. 9A is a side view of a unibody support member, according to yet another embodiment.
Figure 9B:
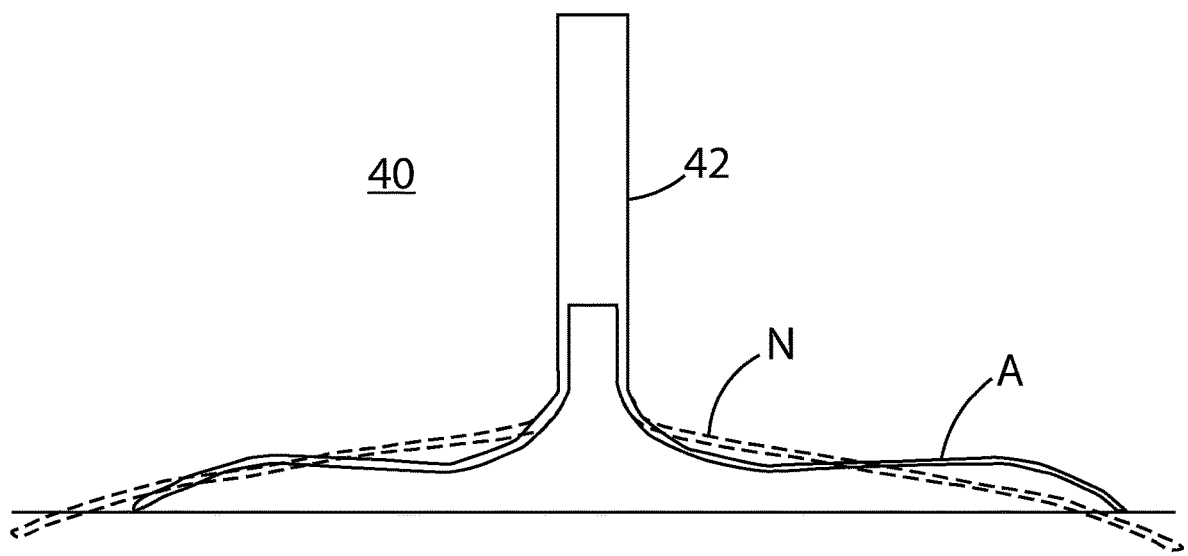
FIG. 9B is a side view of the unibody support member of FIG. 9A, in tissue contact.

As another example, as shown in FIG. 9A, one or spines 17D have a first segment SJ with preformed curvature CJ defined by radius RJ, a second segment SK that is linear, and a third segment SL with preformed curvature CL defined by radius RL, wherein radius RJ<radius RL. As shown in FIG. 9B (with only two spines shown for purposes of clarity), when the spine distal ends come in contact with an illustrative surface SF, the preformed spines transition from their neutral configuration N into their adaptive or temporarily "deformed" configuration A which may include a lower profile (compared to their neutral configuration) that may be better suited for a flatter region of heart tissue.

Figure 10:
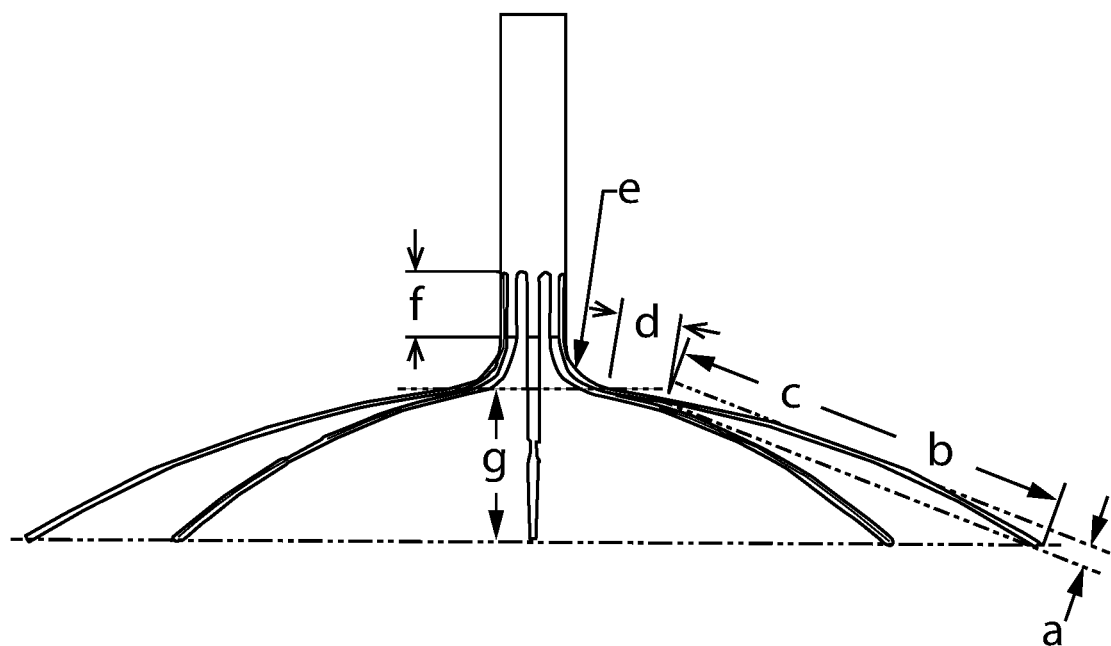
FIG. 10 is a side view of a unibody support member, according to one embodiment, illustrated to show different parameters.

With reference to FIG. 10, in some embodiments, the unibody support member 40 and its spines 17 can be defined by a plurality of parameters, including the following, for example:

a=height of second curvature, ranging between about 0.00" and 0.050"

b=distal length of second curvature, ranging between about 0.302" and 0.694"

c=proximal length of second curvature, ranging between about 0.00" and 0.302"

d=distance between first and second curvature, ranging between about 0.00" and 0.170"

e=radius of first curvature, ranging between about 0.075" and 0.100"

f=length of uniform width segment, being about 0.100"

g=concavity depth, ranging between about 0.123" and 0.590"

Notably, in some embodiments of the unibody support member 40, the proximal (or first) preformed curvature is opposite of the distal (or second) preformed curvature so the spines 17 of the distal electrode assembly 15 can maintain its general concavity and remain forward-facing upon tissue contact, without inverting, while the highly-flexible spines allow the assembly to have a pliability or "give" that prevents the distal tips of the spines from perforating or otherwise causing damage to tissue upon contact and when the distal electrode assembly is pressed toward the tissue surface to ensure tissue contact by each of the spines 17. Moreover, in some embodiments, the indented portion 50 may span between the proximal and distal preformed curvatures so that each of three portions (proximal, indented and distal) of the spines can behave differently and have a degree of independence in flexibility of each other in response to tissue contact and the associated pressures applied by the operator user of the catheter.

It is understood that the foregoing figures illustrate exaggerated deformities and curvatures of the spines for ease of discussion and explanation, whereas actual deformities and curvatures may be much more subtle and less acute.

Figure 11A:
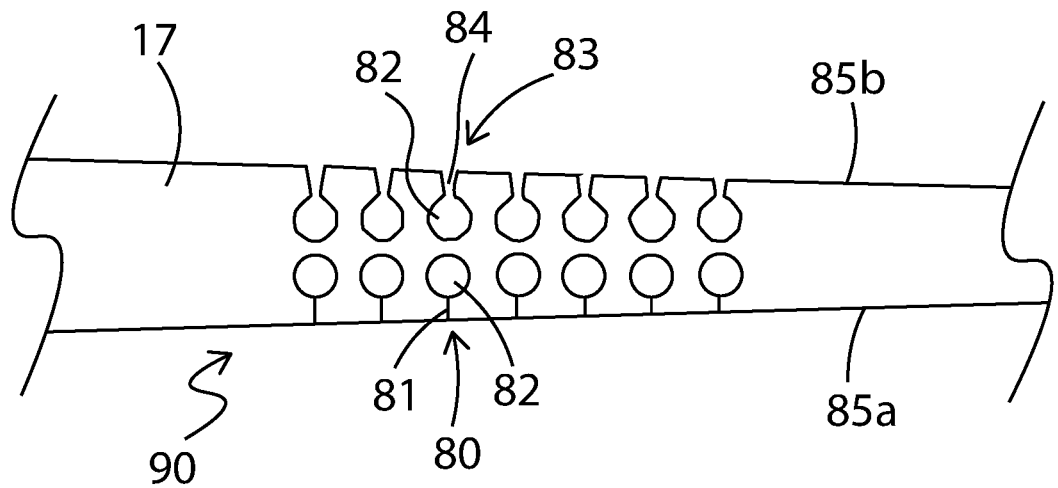
FIG. 11A is a top plan view of a spine with hinge formations, according to one embodiment.
Figure 11B:
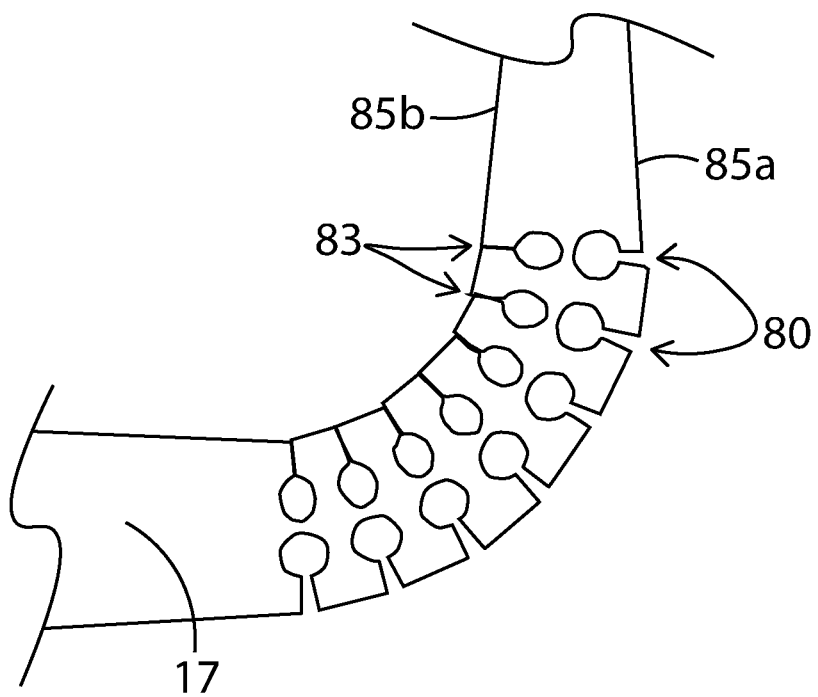
FIG. 11B is a top plan view of a spine with hinge formations, according to another embodiment.

In some embodiments, one or more spines 17 are also configured with a hinge 90 for in-plane (side-to-side) deflection. As shown in FIG. 11A and FIG. 11B, a spine 17 can have a plurality of notches or recesses along opposing lateral edges, including expandable recess 80 (e.g., in the form of slits 81 and circular openings 82) along one edge 85a and compressible recess 83 (e.g., in the form of slots 84 and circular openings 82) along an opposite edge 85b, forming a hinge 90 for more in-plane deflection along those edges. In the embodiments of FIG. 11A and FIG. 11B, uni-deflection occurs toward the edge 85b of the spine 17. However, it is understood that where compressible recess 83 are formed along both the edges 85a and 85b the spine 17 has bi-directional deflection toward either edge 85a or 85b. Suitable hinges are described in U.S. Pat. No. 7,276,062, the entire content of which is incorporated herein by reference.

Figure 12A:
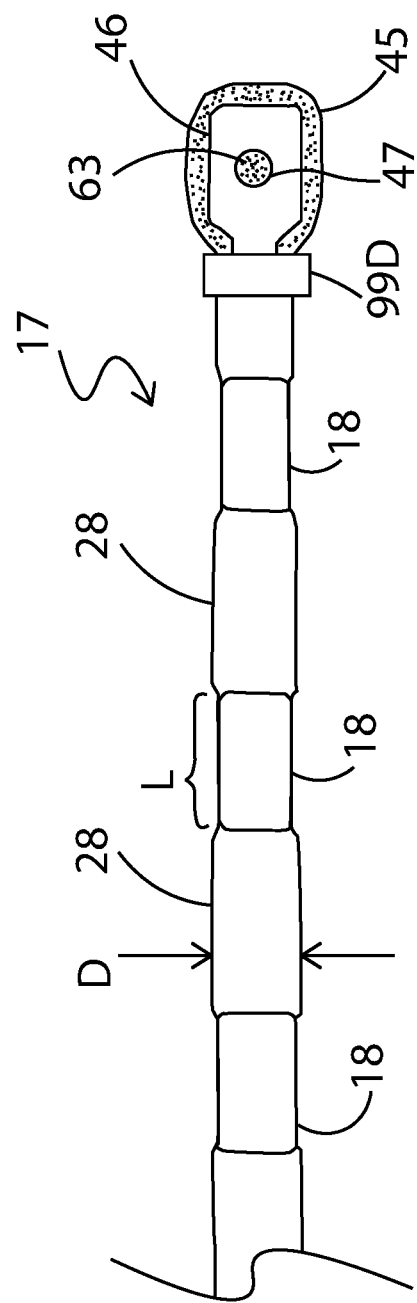
FIG. 12A is a side view of a covered spine, according to one embodiment.
Figure 12B:
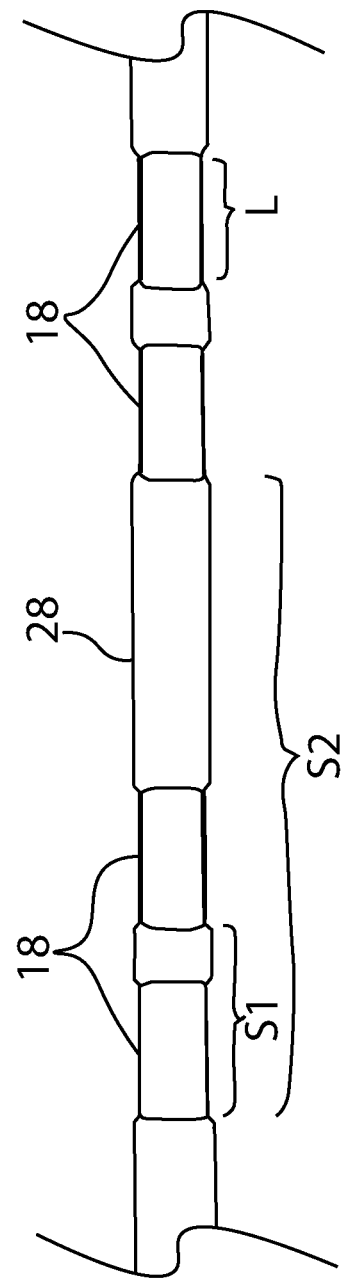
FIG. 12B is a side view of a covered spine, according to another embodiment.

As shown in FIG. 12A and FIG. 12B, each spine 17 of the distal electrode assembly 15 is surrounded along its length by a non-conductive spine cover or tubing 28. In some embodiments, the non-conductive spine cover 28 comprises a very soft and highly flexible biocompatible plastic, such as PEBAX or PELLATHANE, and the spine cover 28 is mounted on the spine with a length that is coextensive with the spine as between the stem 42 and the enlarged distal portion 46. A suitable construction material of the spine cover 28 is sufficiently soft and flexible so as generally not to interfere with the flexibility of the spines 17.

In some embodiments, each covered spine 17 along its length has a diameter D of less than 3 french, preferably a diameter of less than 2.7 french, and more preferably a diameter of 2 french, (e.g., between about 0.025" and 0.035" in diameter).

Each spine 17 at includes an atraumatic distal cover or cap 45 (see FIG. 12A) encapsulating the enlarged distal portion

46. In some embodiments, the cover 45 comprises an biocompatible adhesive or sealant, such as polyurethane, which has a bulbous configuration to minimize injury to tissue upon contact or the application of pressure against tissue. The formation of the cover 45 includes a bridging portion 63 of the adhesive or sealant that passes through the through-hole 47 in the enlarged distal portion 46 and advantageously creates a mechanical lock that secures the cover 45 on the distal portion 46 and minimizes the risk of the cover 45 detaching from the enlarged distal portion 46.

Each spine 17 carries a plurality of microelectrodes 18. The plurality and arrangement of microelectrodes can vary depending on the intended use. In some embodiments, the plurality ranges between about 48 and 72, although it is understood that the plurality may be greater or lesser. In some embodiments, each microelectrode has a length L of less than 800 µm, for example, ranging between about 600 µm and 300 µm, and, for example, measuring about 480 µm, 460 µm or about 450 µm. In some embodiment, the distal electrode assembly 15 has an area coverage greater than about 7.1 cm$^2$, for example, ranging between about 7.2 cm$^2$ and 12.6 cm$^2$. In some embodiments, the distal electrode assembly 15 has a microelectrode density greater than about 2.5 microelectrodes/cm$^2$, for example, ranging between about 4 microelectrodes/cm$^2$ and 7 microelectrodes/cm$_2$.

In some embodiments, the distal electrode assembly 15 has eight spines, each of about 1.5 cm in length and carrying eight microelectrodes for a total of 48 microelectrodes, each with microelectrode having a length of about 460 µm, wherein the assembly 15 has an area coverage of about 7.1 cm$^2$, and a microelectrode density of about 7 microelectrodes/cm$_2$.

In some embodiments, the distal electrode assembly 15 has eight spines, each of about 2.0 cm in length and carrying six microelectrodes for a total of 48 microelectrodes, each with microelectrode having a length of about 460 µm, wherein the assembly 15 has an area coverage of about 12.6 cm$^2$, and a microelectrode density of about 4 microelectrodes/cm$_2$.

The microelectrodes 18 on a spine 17 may be arranged with a variety of spacing between them as either monopoles or bipoles, with the spacing measured as the separation between respective leading edges of adjacent microelectrodes or microelectrode pairs. As monopoles, the microelectrodes 18 can be separated by a distance S1 ranging between about 1 mm and 3 mm, with reference to FIG. 12A. As bipoles, adjacent pairs of microelectrodes 18 can be separated by a distance S2 ranging between 1 mm and 6 mm, with reference to FIG. 12B.

In some embodiments, six microelectrodes are arranged as three bipole pairs, with a spacing S1 of 2.0 mm between proximal edges of a bipole pair, and a spacing S2 of 6.0 mm between proximal edges of adjacent bipole pairs, with reference to FIG. 12B, which may be referred to generally as a "2-6-2" configuration. Another configuration, referred to as a "2-5-2-5-2" configuration, has three bipole pairs, with a spacing S1 of 2.0 mm between proximal edges of a bipole pair, and a spacing S2 of 5.0 mm between proximal edges of adjacent bipole pairs.

In some embodiments, six microelectrodes are arranged as monopoles, with a spacing S1 of 2.0 mm between proximal edges of adjacent monopoles, with reference to FIG. 12A which may be referred to as "2-2-2-2-2" configuration. In some embodiments, the space S1 is about 3.0 mm and thus is refereed to as a "3-3-3-3-3" configuration.

Figure 13:
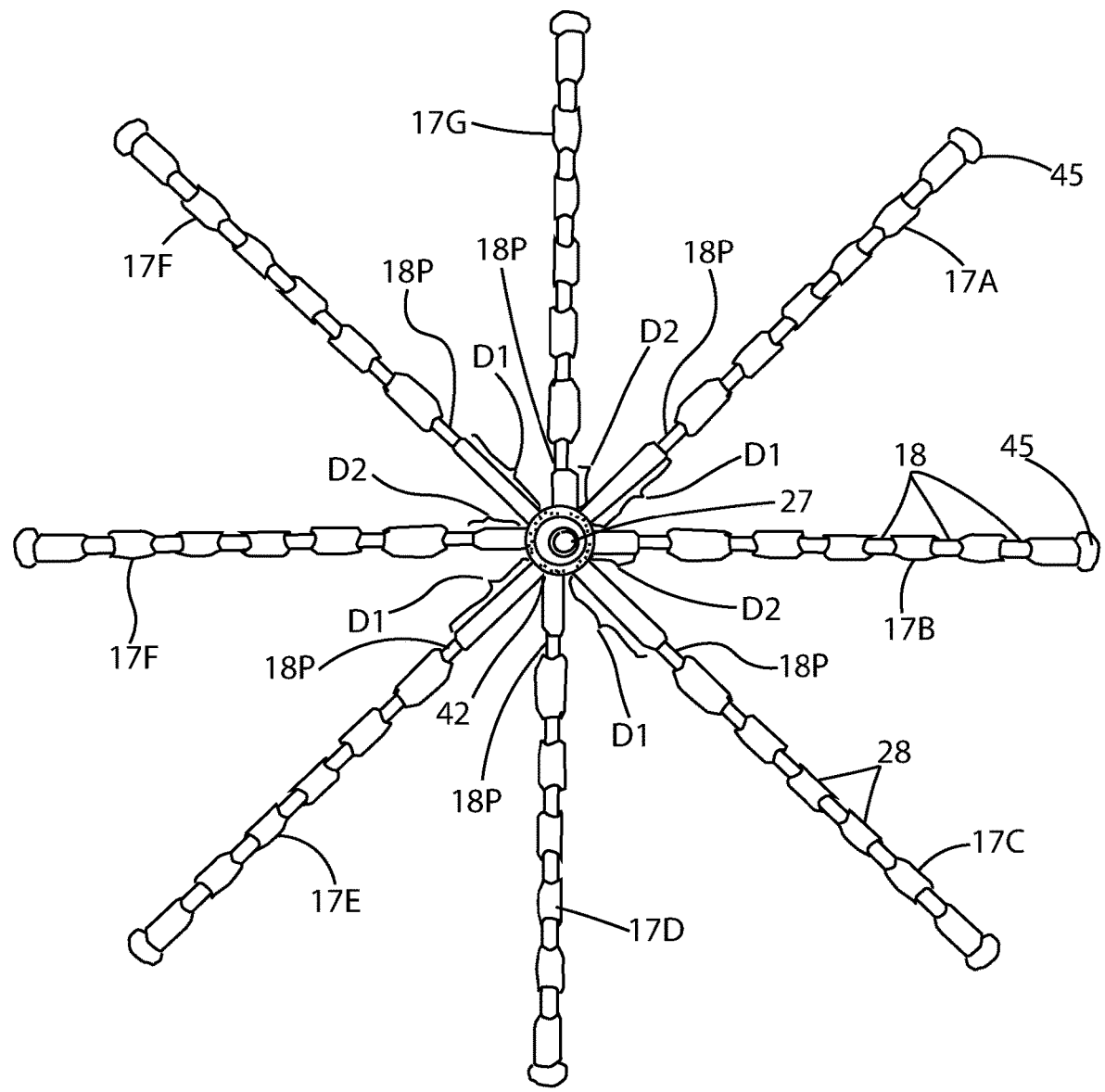
FIG. 13 is a front view of a distal electrode assembly, according to one embodiment.
Figure 26:
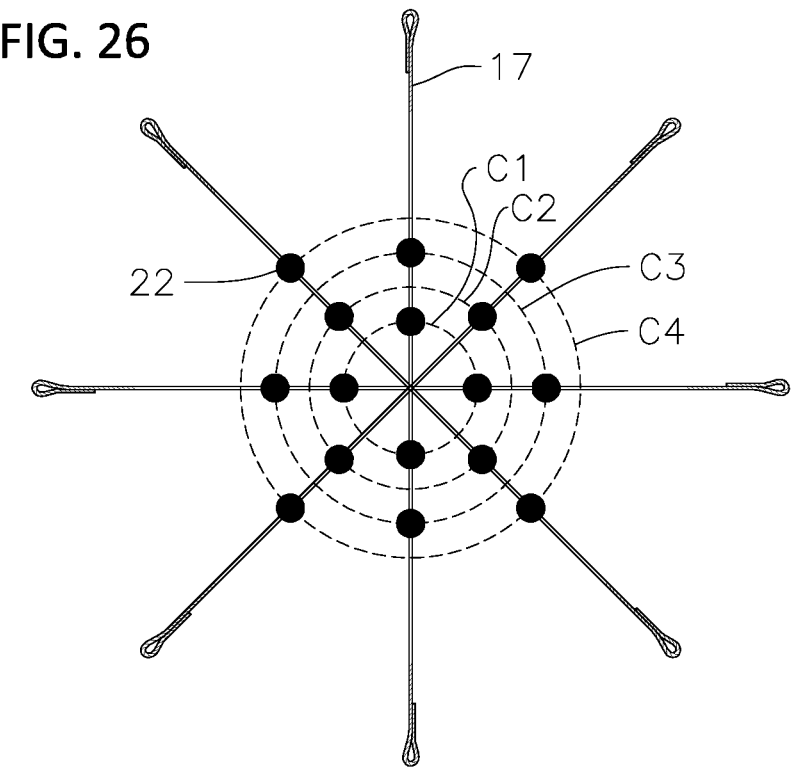
FIG. 26 is a schematic illustration of concentricities a distal electrode assembly, according to one embodiment.
Figure 27:
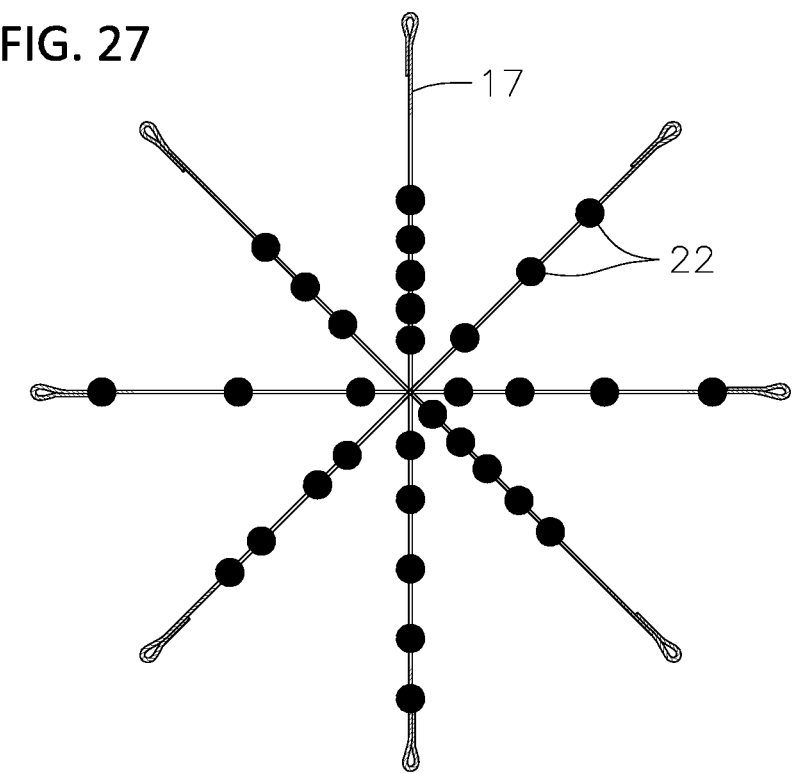
FIG. 27 is a schematic illustration of concentricities of a distal electrode assembly, according to another embodiment.

In some embodiments, the most proximal microelectrode 18P of each spine is carried on the spine at a different location from the most proximal microelectrode 18P of adjacent spines. As illustrated in FIG. 13, whereas the spacing between microelectrodes on any one spine may be uniform throughout the distal electrode assembly, the microelectrodes along any one spine is staggered (or offset) relative to the microelectrodes along adjacent spines. For example, the distance D1 between the most proximal microelectrode 18P and the end of the stem 42 for spines 17A, 17C, 17E and 17G is greater than the distance D2 between the most proximal electrodes 18P and the end of the stem 42 for spines 17B, 17D, 17G and 17G. This staggered configuration minimizes the risk of microelectrodes on adjacent spines from touching and shorting, especially when an operator sweeps the distal electrode assembly against tissue. Moreover, the staggered configuration provides a greater effective contact surface of the distal electrode assembly 15 because the effective concentric electrode arrays is doubled (see FIG. 13). With reference to FIG. 13, FIG. 26 and FIG. 27, staggering can assume different configurations depending on factors, including the distance or spacing between adjacent electrodes on any one spine. In some embodiments, each spine can assume a unique staggered configuration (FIG. 27). In some embodiments, one or more spines can assume the same staggered configuration so long as these spines are not adjacent to each other and are separated by at least one or more spines with a different staggered configuration (see, for example, concentricities C1, C2, C3 and C4 in FIG. 26). In this regard, spacing between adjacent electrodes along any one spine may be nonuniform, so long as the spacing between adjacent electrodes along an adjacent spine is different and the electrodes of adjacent spines lie on different concentricities. Staggered configuration also includes configuration whereby concentric tracings about the longitudinal axis of the assembly 15 of the electrodes of any one spine are different from the concentric tracings of the electrodes of any adjacent spines.

Figure 14A:
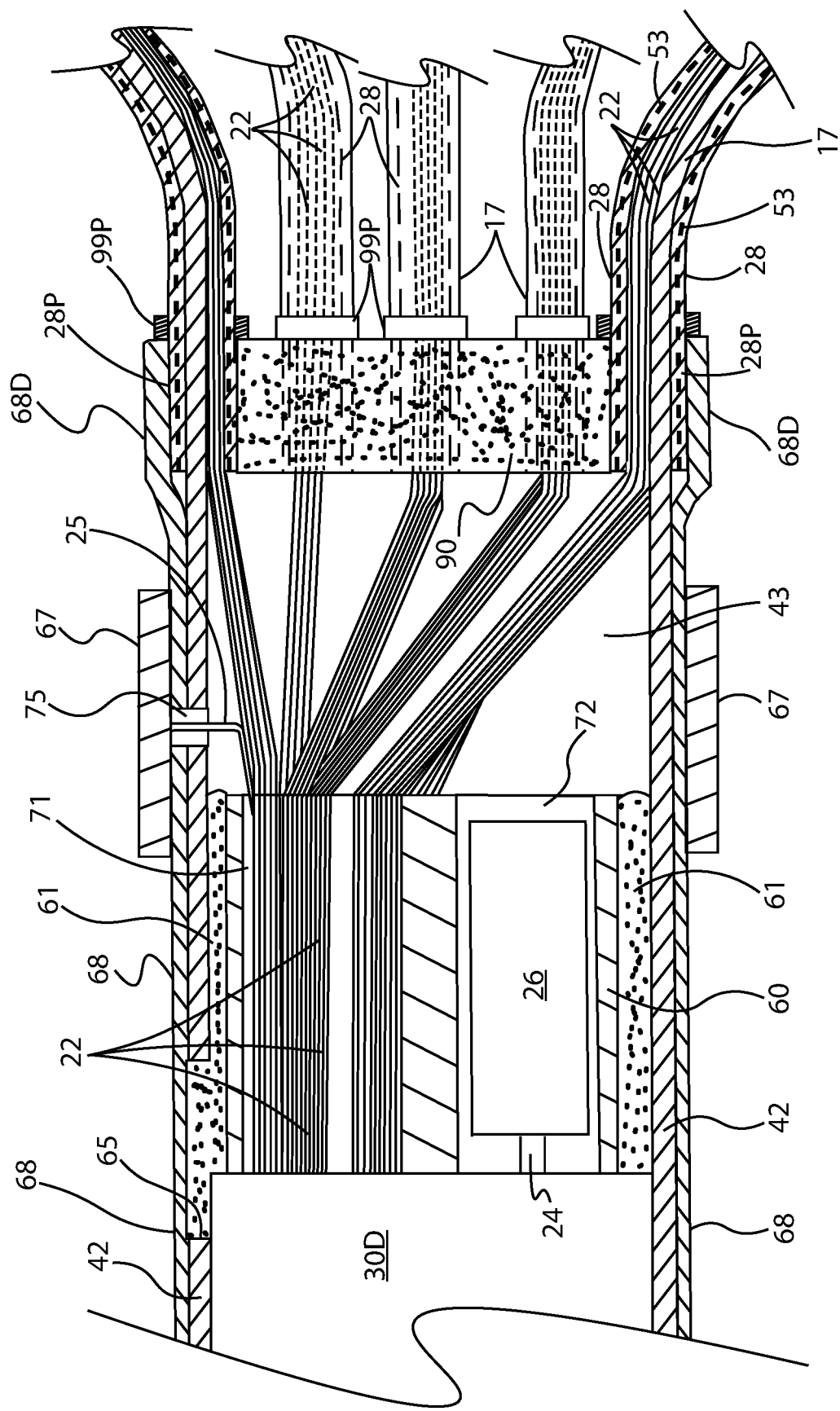
FIG. 14A is a side cross-sectional view of a junction between a deflection section and a distal electrode assembly, according to one embodiment.

Components of construction and assembly of the junction between the distal electrode assembly and the distal end portion of the deflection section 14 are described in U.S. Pat. Nos. 7,089,045, 7,155,270, 7,228,164, and 7,302,285, the entire disclosures of which are incorporated herein by reference. As shown in FIG. 14A, the stem 42 of the unibody support member 40 receives a narrowed distal end 30D of the multi-lumened tubing 30 of the deflection section 14. Surrounding the stem 42 circumferentially is a nonconductive sleeve 68 that is coextensive with the stem between its proximal end and its distal end. Distal end 68D of the sleeve 68 extends over the proximal ends 28P of the nonconductive spine tubings 28 so as to help secure the tubings 28 on the spines 17.

Figure 14B:
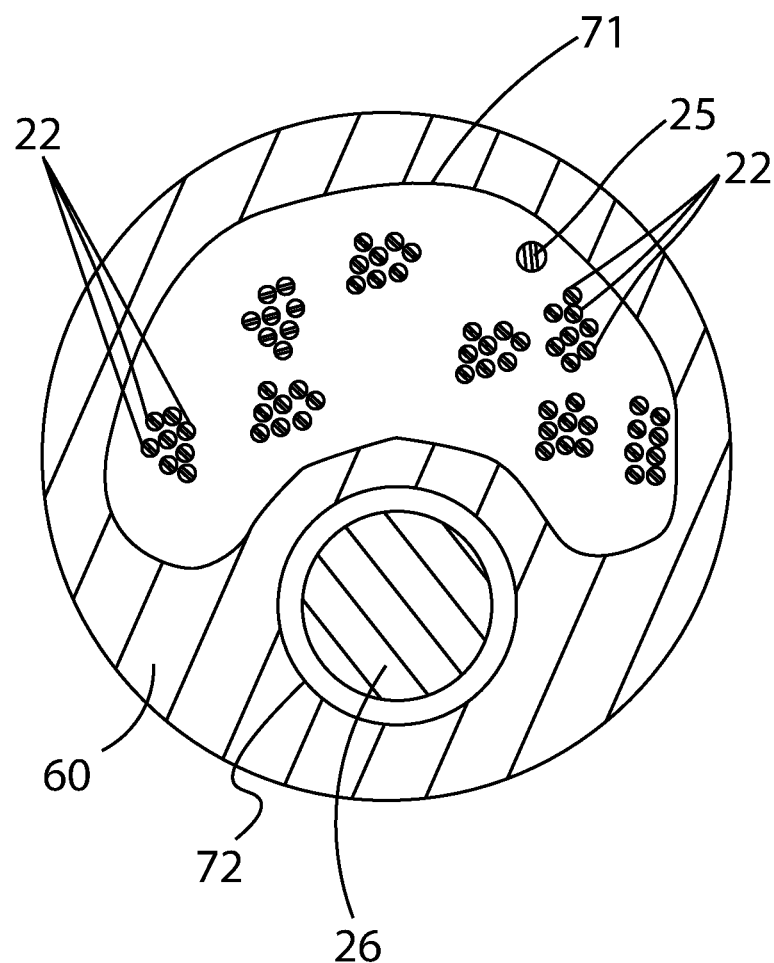
FIG. 14B is an end cross-sectional view of a housing insert of FIG. 14A.

Proximal of the distal end 30D is a housing insert 60 that is also received and positioned in the lumen 43 of the stem 42 of the unibody support member 40. The housing insert 60 has a length in the longitudinal direction that is shorter than the length of the stem 42 so that it does not protrude past the distal end of the stem 42. The housing insert 60 is configured with one or more lumens. One lumen 71 may have a noncircular cross-section, for example, a cross-section that generally resembles a "C" or an elongated kidney-bean, and another lumen 72 may have a circular cross-section, as shown in FIG. 14B, so that the lumens can nest with each other to maximize the size of the lumens and increase space efficiency within the housing insert 60. Components passing through the lumen 71 are not trapped in any one location or position and thus have more freedom to move and less risk of breakage, especially when segments of the catheter are torqued and components are twisted.

In some embodiments, the electromagnetic position sensor 26 (at the distal end of the cable 24) is received in the lumen 72. Other components including, for example, the irrigation tubing 27, and the lead wires 22 for the microelectrodes 18 on the distal electrode assembly 15 (and lead wires 25 for any ring electrodes 67, 69, and 70 proximal of the spines 17) pass through the lumen 71. In that regard, the housing insert 60 serves multiple functions, including aligning and positioning the various components within the stem 42 of the unibody support member 40, provides spacing for and separation between these various components, and serves as a mechanical lock that reinforces the junction between the distal end of the deflection section 14 and the distal electrode assembly 15. In the latter regard, the junction, during the assembly and use of the catheter, can be subject to a variety of forces that can torque or pull on the junction. Torque forces, for example, can pinch the irrigation tubing 27 to impede flow, or cause breakage of the lead wires 22 and 25. To that end, the junction is advantageously assembled in a configuration with the housing insert 60 to form a mechanical lock, as explained below.

The housing insert 60 may be selectively configured with an outer diameter that smaller than the inner circumference of the lumen 43 of the stem 42 by a predetermined amount. This creates an appreciable void in the lumen 43 that is filled with a suitable adhesive 61, such as polyurethane, to securely affix the housing insert 60 inside the lumen 43 and to the distal end of the multi-lumened tubing 30 so as to minimize, if not prevent, relative movement between the insert 60 and the stem 42. The housing insert 60 protects the components it surrounds, including the electromagnetic position sensor 26 (and its attachment to the cable 24), the irrigation tubing 27, and the lead wires 22 and 25, and provides a larger and more rigid structure to which the stem 42 is attached. To that end, the housing insert 60 may even have a noncircular/polygonal outer cross-section and/or a textured surface to improve the affixation between the housing insert 60 and the adhesive 61.

To facilitate the application of the adhesive into the void, the stem 42 is formed with an opening 65 in its side wall at a location that allows visual and mechanical access to the housing insert 60 after it has been inserted into the lumen 43 of the stem 42. Visual inspection of the lumen 43 and components therein during assembly of the junction is provided through the opening 65. Whereas any adhesive applied to the outer surface of the housing insert 60 before insertion into the lumen 43 may squirt out of the stem 42 during insertion, additional adhesive may be advantageously applied into the lumen 43 through the opening 65 to fill the void and thus securely affix the housing insert 60 to the stem 42 and the distal end portion of the multi-lumened tubing 30. The combination of the housing insert 60 and its spatially-accommodating lumen 71 provides a more integrated and less vulnerable junction between the distal electrode assembly 15 and the deflection section 14.

Figure 15A:
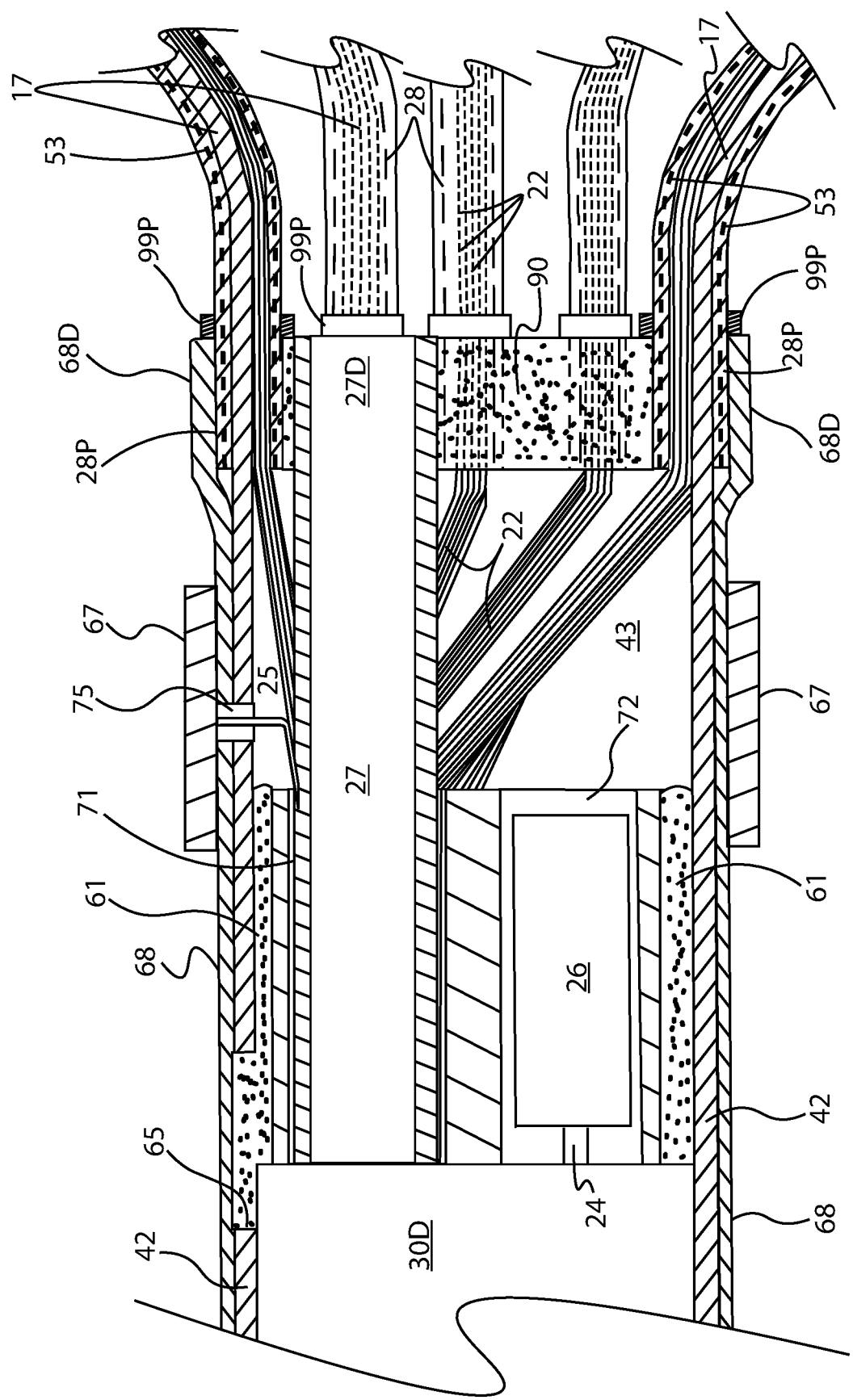
FIG. 15A is a side cross-sectional view of a junction between a deflection section and a distal electrode assembly, according to another embodiment.
Figure 15B:
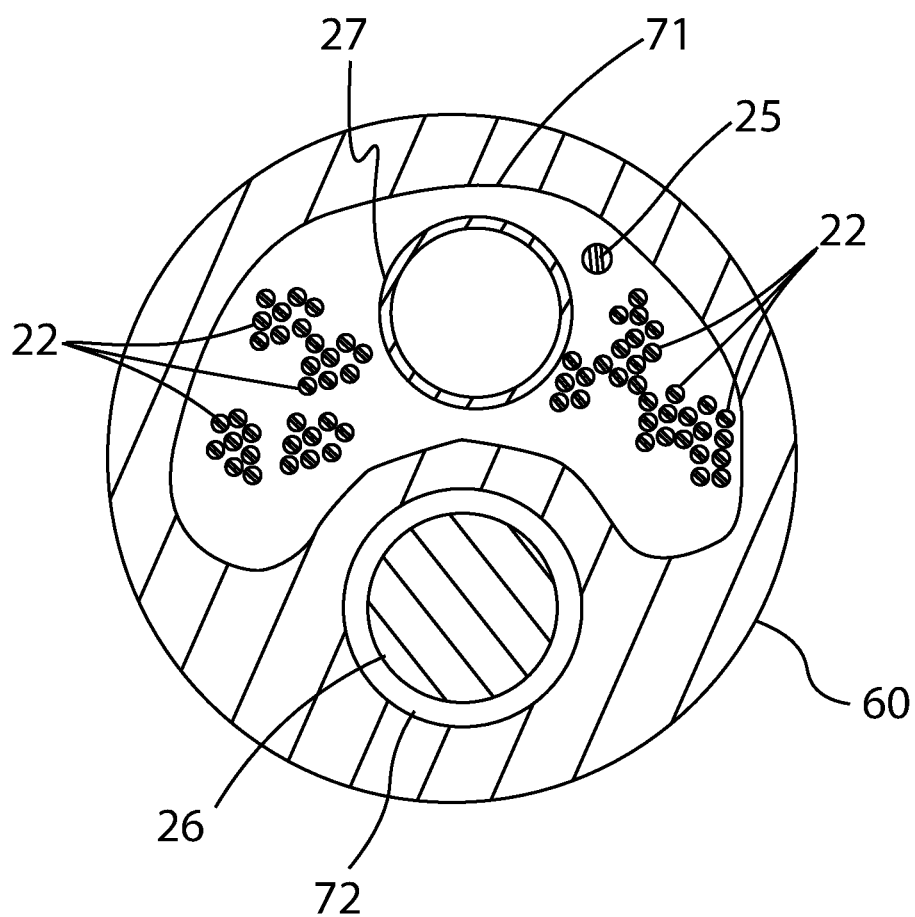
FIG. 15B is an end cross-sectional view of a housing insert of FIG. 15A.
Figure 25:
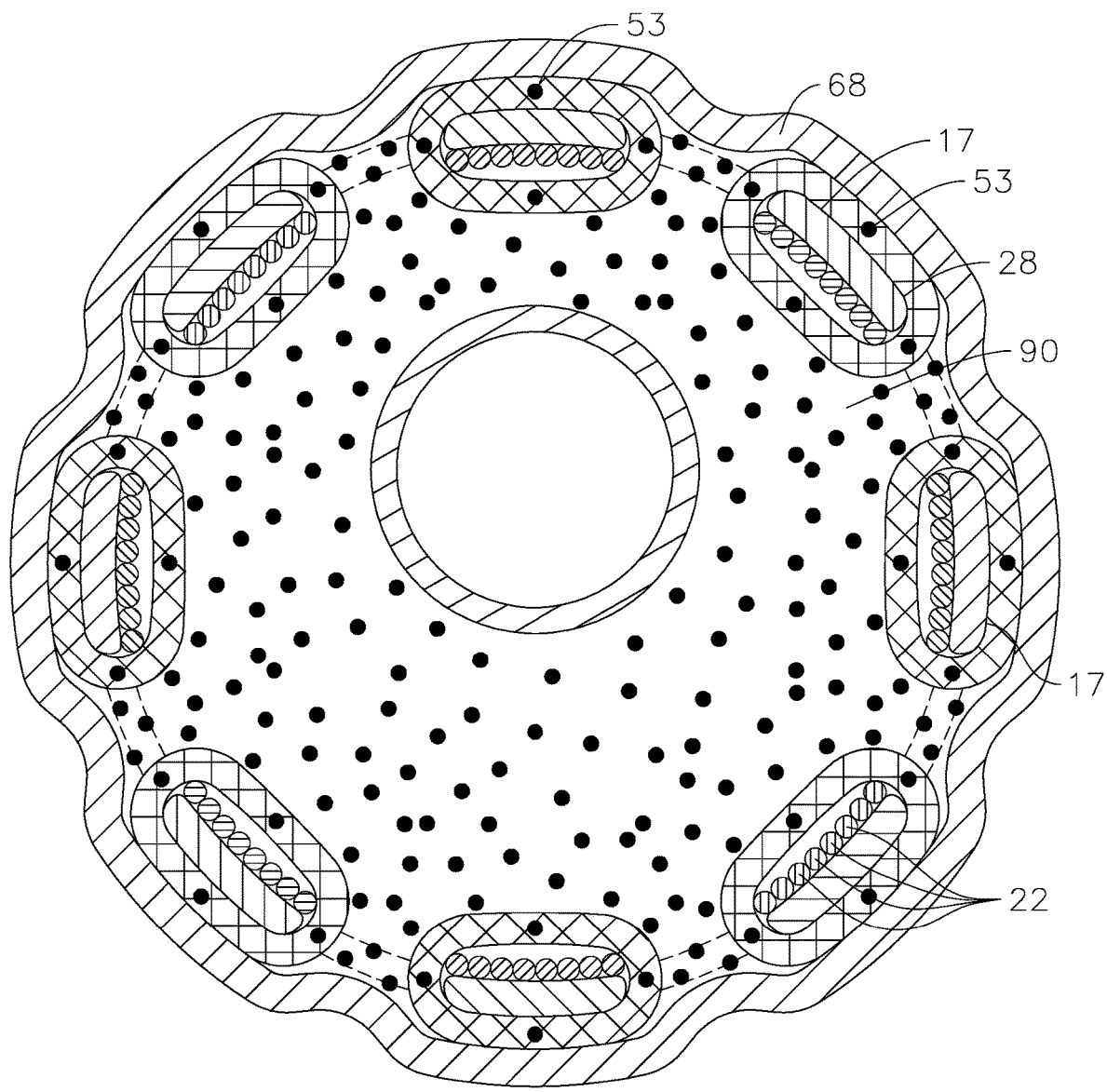
FIG. 25 is an end cross-sectional view of the distal end of the distal electrode assembly of FIG. 15A, taken along line A-A.

In some embodiments, the catheter 10 includes the irrigation tubing 27 whose distal end 27D is generally coextensive with the distal end of the stem 42 of the unibody support member 40. As such, irrigation fluid, e.g., saline, is delivered to the distal electrode assembly 15 from a remote fluid source that provides irrigation fluid via a luer hub 100 (FIG. 1) via the irrigation tubing 27 that extends through the control handle 16, the center lumen 19 of the catheter body 12 (FIG. 2), and the lumen 31E of the tubing 30 of the deflection section 14 (FIG. 3), where it exits the distal end of the irrigation tubing 27 at the distal end of the stem 42 of the unibody support member 40, as shown in FIG. 15A and FIG. 25. A suitable adhesive, such as polyurethane, plugs and seals the lumen 43 around the distal end of the irrigation tubing 27. In some embodiments, the catheter is without irrigation and the distal end of the stem 42 of the unibody support member 40 is sealed in its entirety by the adhesive or sealant 90, such as polyurethane, as shown in FIG. 14A.

Figure 16:
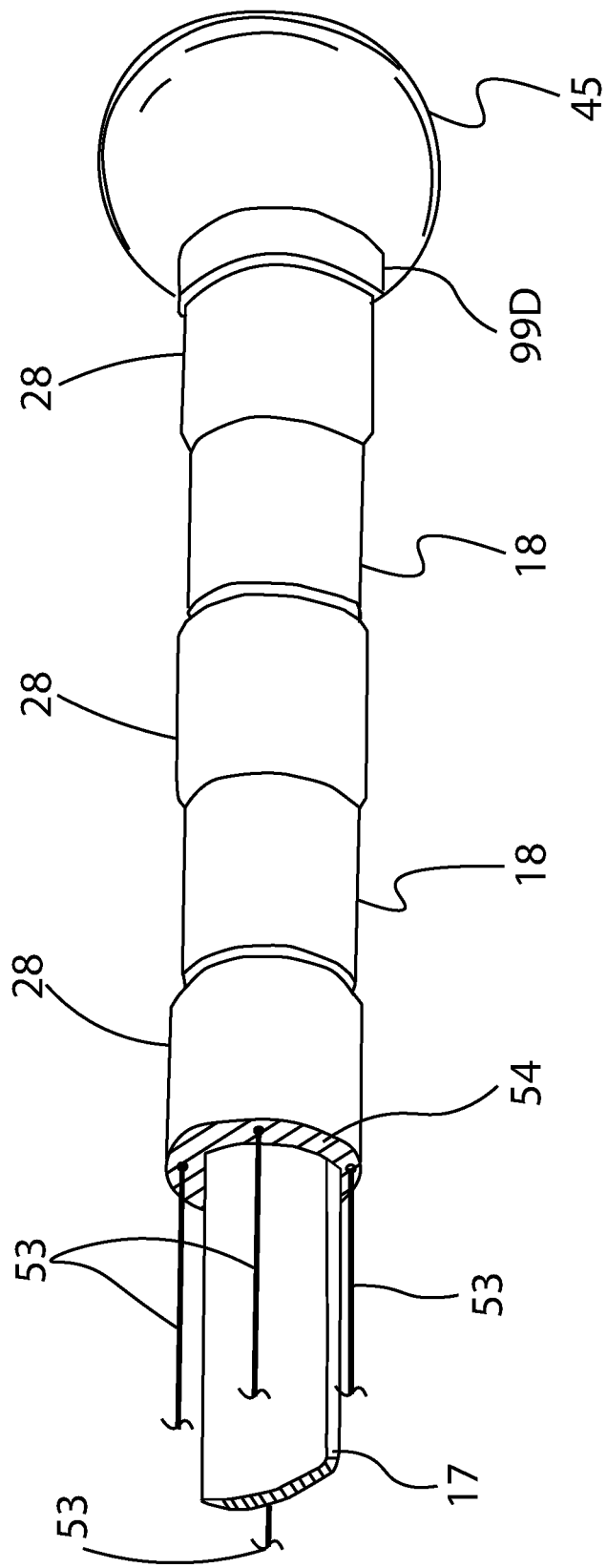
FIG. 16 is a side perspective view of a covered spine with reinforcing tensile members, according to one embodiment.
Figure 17:
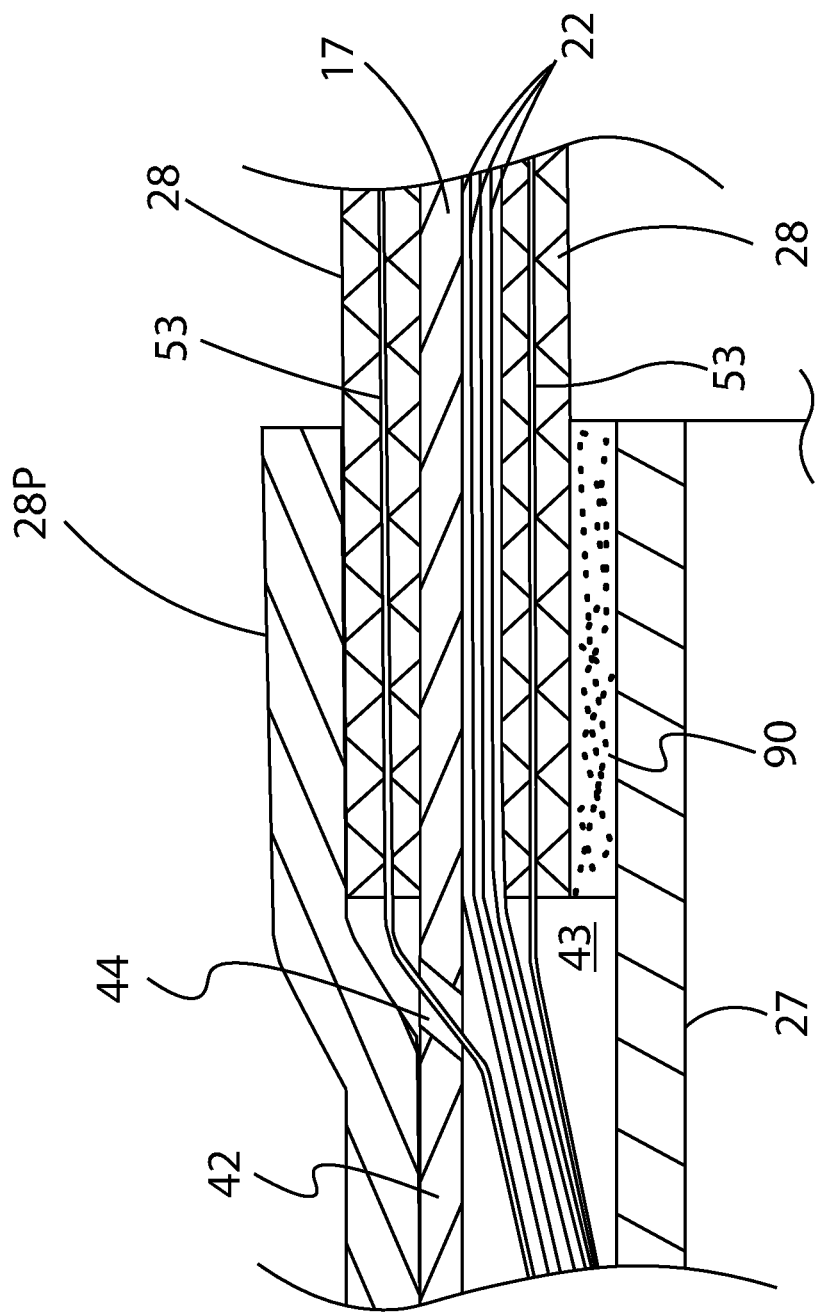
FIG. 17 is a detailed side cross-sectional view of a portion of a junction with reinforcing tensile members, according to one embodiment.
Figure 18:
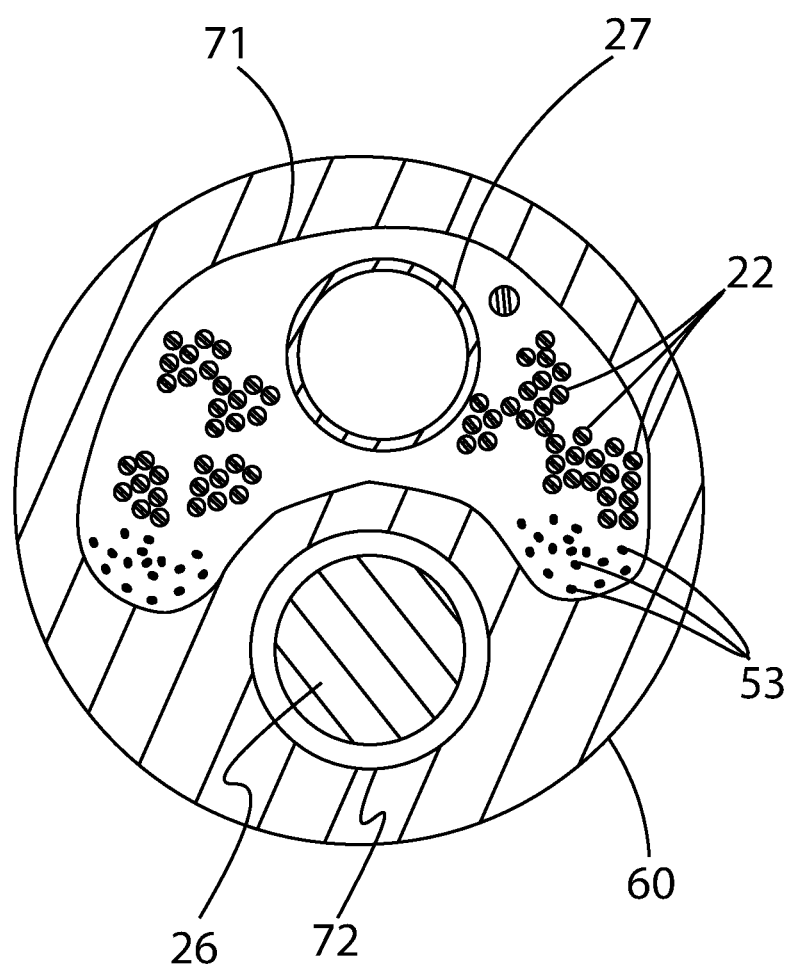
FIG. 18 is an end cross-sectional view of a housing insert with reinforcing tensile members passing therethrough, according to one embodiment.
Figure 19:
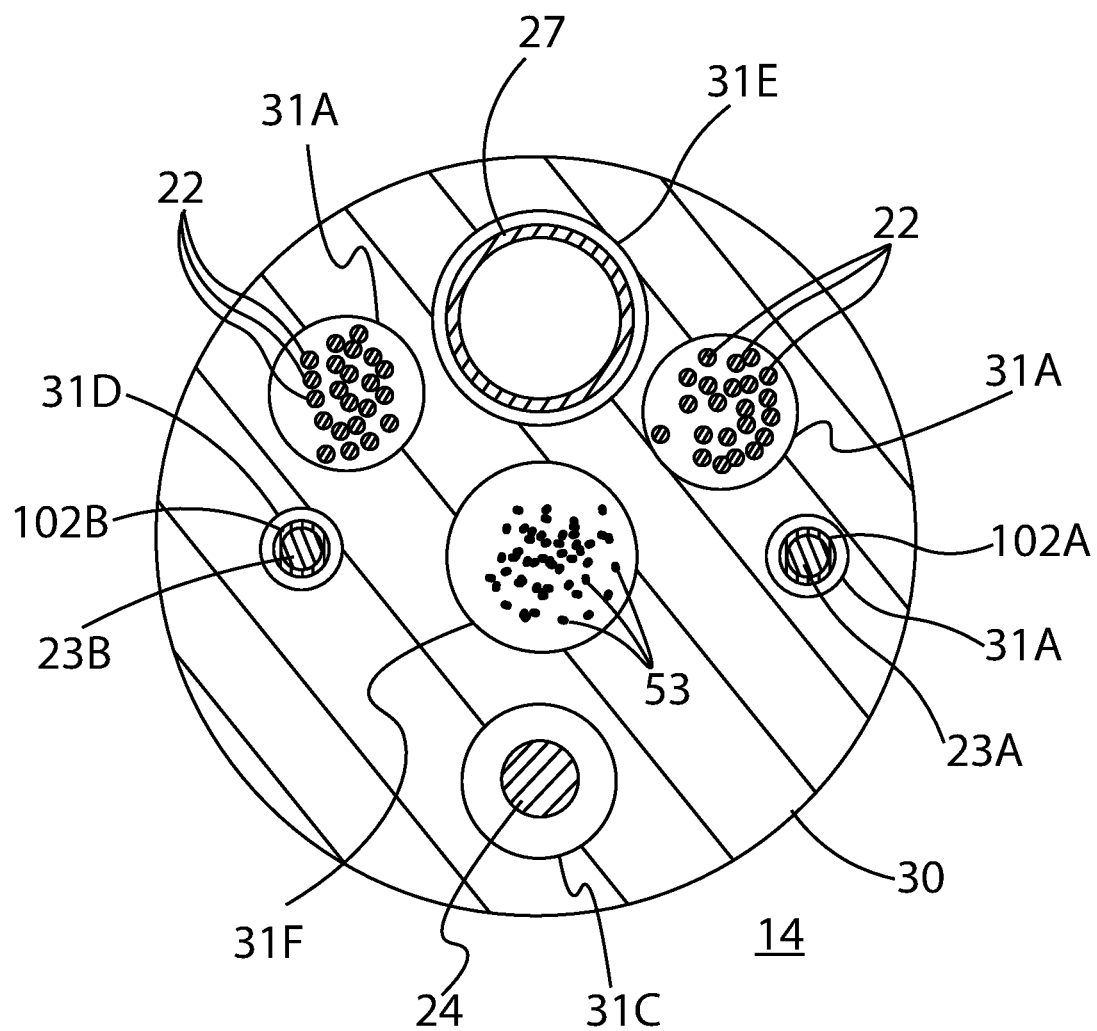
FIG. 19 is an end cross-sectional view of a deflection section with reinforcing tensile members passing therethrough, according to one embodiment.
Figure 20:
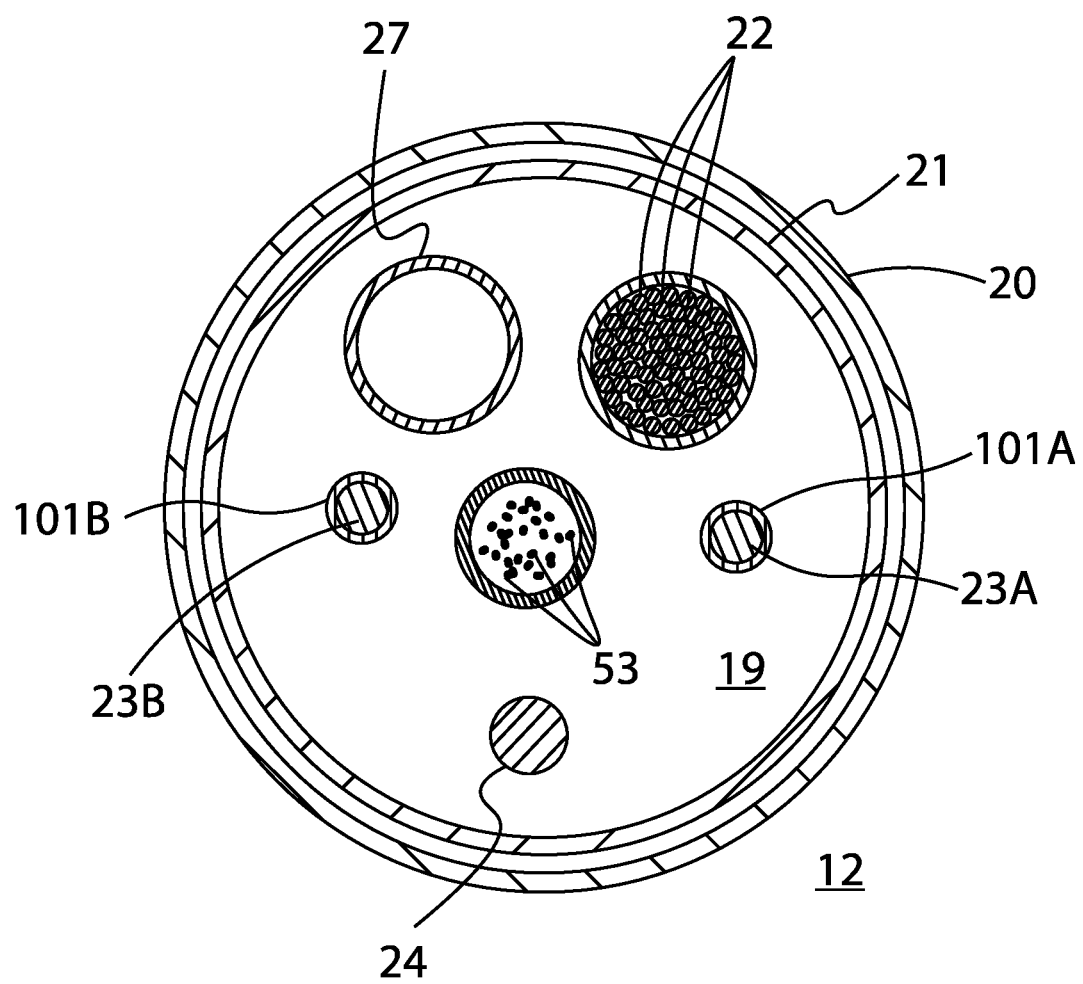
FIG. 20 is an end cross-sectional view of a catheter body with reinforcing tensile members passing therethrough, according to one embodiment.
Figure 21:
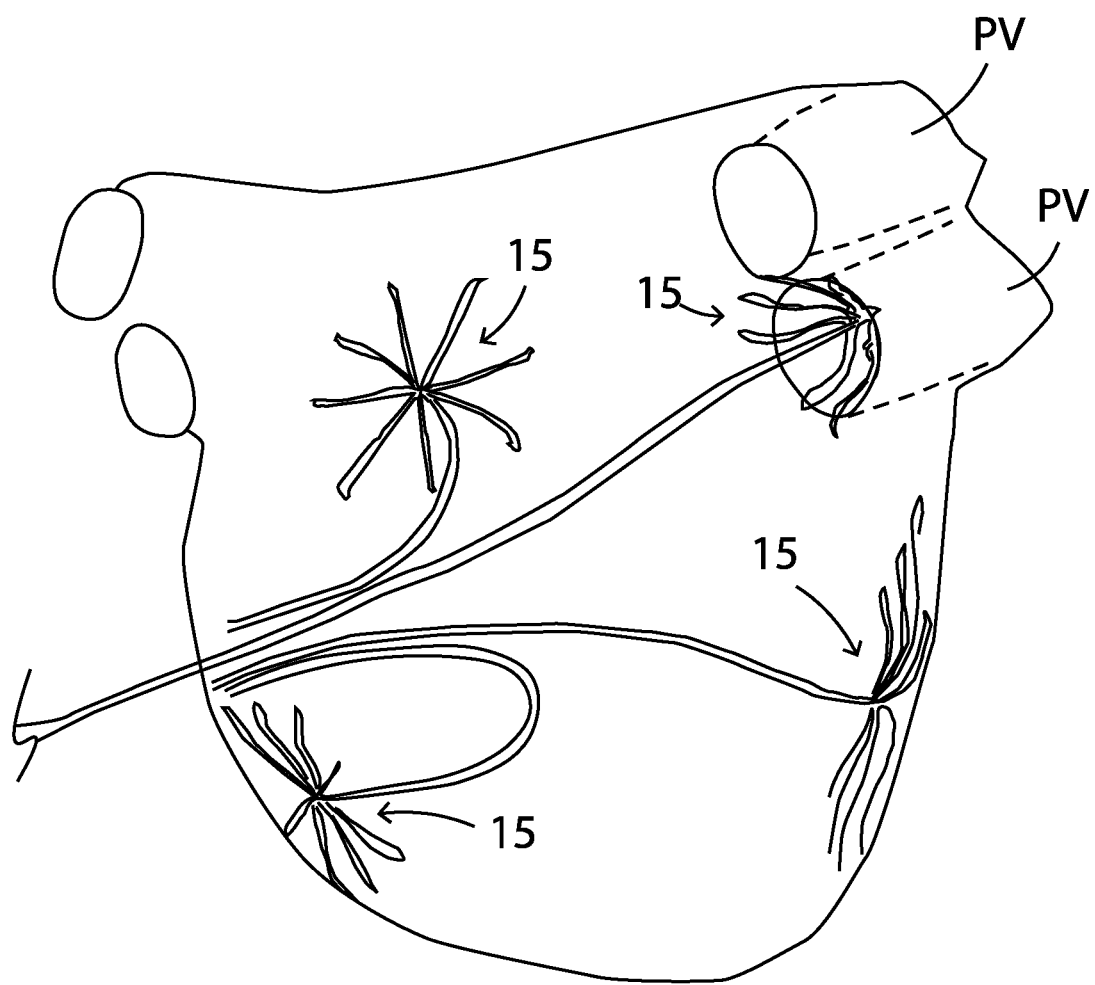
FIG. 21 is a schematic illustration of a heart and placement of the catheter of the present invention for tissue contact, according to various embodiments.
Figure 22:
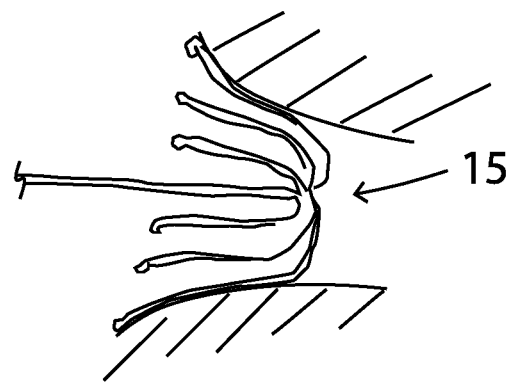
FIG. 22 is a schematic illustration of a distal electrode assembly in contact with tissue in a pulmonary vein, according to one embodiment.
Figure 23:
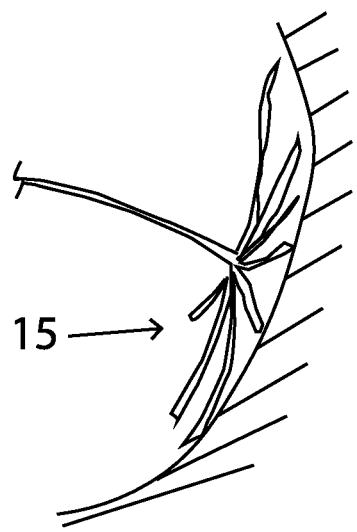
FIG. 23 is a schematic illustration of a distal electrode assembly in contact with tissue of a lateral wall of the heart, according to one embodiment.
Figure 24:
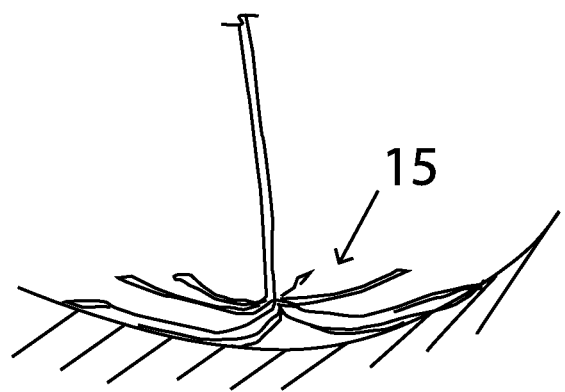
FIG. 24 is a schematic illustration of a distal electrode assembly in contact with tissue of an inferior wall or apex of the heart, according to one embodiment.

FIG. 16 illustrates an embodiment wherein the nonconductive spine tubings 28 include reinforcing tensile members 53. As understood by one of ordinary skill in the art, the microelectrodes 18 are mounted on the spine cover or tubing 28 wherein an elongated tubular mandrel (not shown) is positioned in the lumen of the spine cover 28 to support the microelectrodes 18 while they are rotationally swaged onto the spine cover 28. The microelectrodes 18 may have a circular cross-section, including the configuration of a circle or an oval. To prevent or at least minimize undesirable deformation of the microelectrodes 18 and the spine cover 28 during swaging, including elongation in the longitudinal direction, the spine cover 28 on which the microelectrodes are carried and swaged onto includes reinforcing tensile members 53, as shown in FIG. 16. Tensile members 53, for example, wires or fibers (used interchangeably herein), are embedded (for example, during extrusion of the tensile members) in the side wall 54 of the tubing. The tensile members 53 may be embedded in the nonconductive cover extrusion in a uniaxial or braided pattern, extending in the longitudinal direction or at least having portions extending in the longitudinal direction. As such, the tensile members serve to resist undesirable elongation of particularly soft and flexible spine cover 28 and the microelecrodes 18 in the longitudinal direction. Examples of suitable tensile members include VECTRAN, DACRON, KEVLAR or other materials with low elongation properties. The plurality of the reinforcing tensile members is not critical. In some embodiments, the plurality may range between two and six that are arranged in an equi-radial configuration. In the illustrated embodiment, the spine cover 28 includes four tensile members at 0, 90, 180 and 270 degrees about the side wall 54.

In some embodiments, distal ends of the tensile members 53 are anchored in the bulbous cover 45 encapsulating the enlarged distal portion of the spines 17 and/or rings 99D, as shown in FIG. 16, may be compressed or clamped on over the spine cover 28 and spine 17. In some embodiments, proximal ends of the tensile members 53 are coextensive with the proximal end of the spine cover 28, and may also be anchored by rings 99P (see FIG. 14A and FIG. 15A).

In some embodiments, the tensile members 53 have a much greater length. With reference to FIG. 17, FIG. 18, FIG. 19 and FIG. 20, the tensile members 53 extend through openings 44 formed in the stem 42 of the unibody support member 40 and into the lumen 43 of the stem 42. The tensile members 53 then extend through the lumen 71 of the housing insert 60, a lumen 31F of the tubing 30 of the deflection section 14, and the center lumen 19 of the catheter body 12, and into the control handle 16. Proximal ends of the tensile members 53 are configured for manipulation by an operator to deflect the spines 17 of the distal electrode assembly 15 so they can individually function as "fingers." In that regard, the tensile members may be formed in the side wall of the tubing 28 in a manner that allows longitudinal movement relative to the tubing 28 so that any one or more tensile members can be drawn proximally to bend or deflect the respective spine toward the side along which those tensile members extend. As such, an operator is able to manipulate one or more spines for individual deflection as needed or desired, including when the distal electrode assembly is in contact with an uneven tissue surface where one or more spines need adjustment for better tissue contact.

With reference to FIG. 21, FIG. 22, FIG. 23 and FIG. 24, the catheter 10 of the present invention is shown in use in all four chambers of the heart, namely, the left and right atria and the left and right ventricles, with the spines of the distal electrode assembly 15 readily adapting and conforming to various contours and surfaces of the heart tissue anatomy, including, for example, inside a pulmonary vein, and on the posterior wall of the right atrium, and the anterior, inferior and/or lateral walls of the left and right ventricles, and the apex. The preformed configurations of the spines advantageously facilitate contact between the microelectrodes carried on the spines and tissue regardless of the anatomy of the surface.

In some embodiments, the catheter 10 has a plurality of ring electrodes proximal of the distal electrode assembly 15. In addition to the ring electrode 67, as shown in FIG. 1, the catheter carries another ring electrode 69 more proximal than the ring electrode 67, and another ring electrode 70 more proximal than the ring electrode 69. Lead wires 25 are provided for these ring electrodes. In some embodiments, the ring electrode 69 is located near the distal end 30D of the multi-lumened tubing 30 of the deflection section 14, and ring electrode 70 is separated from the ring electrode 69 by a distance S ranging between about 1 mm and 3 mm. A respective lead wire 25 is connected to the ring electrode 67 via opening 75 formed in the stem 42 of the unibody support member 40, and in the sleeve 68. Respective lead wires 25 for ring electrodes 69 and 70 are connected to via openings (not shown) formed in these side wall of the tubing 30 of the deflection section 14.

Each portion of the puller wires 23A and 23B extending through the catheter body 12 is circumferentially surrounded by a respective compression coils 101A and 101B as understood in the art. Each portion of the puller wires 23A and 23B extending through the multi-lumened tubing 30 of the deflection section is circumferentially surrounded by a sheath that protects the puller wires from cutting into the tubing when the puller wires are deflected. Distal ends of the puller wires may be anchored in the sidewall of the tubing 30 at or near the distal end of the tubing 30, as understood in the art. Proximal ends of the puller wires are anchored in the control handle 16 for actuation by the operator of the catheter, as understood in the art.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter comprising:
   an elongated body;
   a distal electrode assembly distal of the elongated body and comprising a support body having:
   a unibody support member having a proximal stem with an inner lumen, and a plurality of spines with diverging distal ends, the spines spanning outwardly from the stem, wherein each spine has a plurality of microelectrodes, each microelectrode defines a concentricity, and the concentricities of the microelectrodes on one spine are different from the concentricities of microelectrodes on adjacent spines; and
   an insert affixed in the inner lumen of the proximal stem, the insert having at least a noncircular lumen through which microelectrode lead wires extend.

2. The catheter of claim 1, wherein the distal electrode assembly comprises at least four first spines and four second spines, and each spine carries six microelectrodes.

3. The catheter of claim 2, wherein the microelectrodes on the first spines have a first separation distance from each other, and the microelectrodes on the second spines have a second separation distance, wherein the first and second separation distances are about the same.

4. The catheter of claim 2, wherein the microelectrodes on the first spines have a first separation distance from each other, and the microelectrodes on the second spines have a second separation distance, wherein the first and second separation distances are different.

5. The catheter of claim 1, wherein the microelectrodes are configured as monopoles.

6. The catheter of claim 1, wherein the microelectrodes are configured as bipoles.

7. The electrophysiology catheter of claim 1, wherein the plurality of microelectrodes carried on each spine is the same.

8. The electrophysiology catheter of claim 1, wherein the plurality of microelectrodes carried on adjacent spines is different.

9. The electrophysiology catheter of claim 1, wherein the plurality of spines is eight.

10. The electrophysiology catheter of claim 1, wherein the plurality of microelectrodes on each spine is six.

11. The electrophysiology catheter of claim 1, wherein the plurality of spines ranges between about six and eight.

12. The electrophysiology catheter of claim 1, wherein the plurality of microelectrodes ranges between about six and eight.

13. The catheter of claim 1, wherein the microelectrodes on each spine are separated by a distance ranging between about 1 mm and 3 mm, as measured between leading edges of the microelectrodes.

14. The catheter of claim 13, wherein the distance is about 2 mm.

15. The catheter of claim 1, wherein the microelectrodes on each spine are arranged as bipole pairs, with leading edges of microelectrodes within a pair separated by a first distance ranging between about 1 mm and 3 mm, and with leading edges of leading microelectrodes between pairs separated by a second distance ranging between 1 mm and 6 mm.

16. The catheter of claim 15, wherein the first distance is about 2 mm and the second distance is about 6 mm.

17. The catheter of claim 1, wherein the plurality of microelectrodes equals about 64.

18. The catheter of claim 1, wherein the plurality of microelectrodes equals about 72.

19. The electrophysiology catheter of claim 1, wherein the noncircular lumen has a generally C-shaped cross-section.

20. The electrophysiology catheter of claim 1, wherein the noncircular lumen has a generally kidney-bean-shaped cross section.

\* \* \* \* \*